United States Patent
Connolly et al.

(10) Patent No.: US 11,278,230 B2
(45) Date of Patent: Mar. 22, 2022

(54) SYSTEMS AND METHODS FOR COGNITIVE HEALTH ASSESSMENT

(71) Applicant: McMaster University, Hamilton (CA)

(72) Inventors: John Francis Connolly, Ancaster (CA); Kyle Ingram Ruiter, Etobicoke (CA); Rober Boshra, Hamilton (CA)

(73) Assignee: MCMASTER UNIVERSITY, Hamilton (CA)

( * ) Notice: Subject to any disclaimer, the term of this patent is extended or adjusted under 35 U.S.C. 154(b) by 8 days.

(21) Appl. No.: 16/513,469

(22) Filed: Jul. 16, 2019

(65) Prior Publication Data

US 2020/0015696 A1  Jan. 16, 2020

Related U.S. Application Data

(60) Provisional application No. 62/698,424, filed on Jul. 16, 2018.

(51) Int. Cl.
| A61B 5/377 | (2021.01) |
| A61B 5/291 | (2021.01) |
| A61B 5/16 | (2006.01) |
| G06N 20/00 | (2019.01) |
| A61B 5/316 | (2021.01) |
| G06N 3/08 | (2006.01) |

(Continued)

(52) U.S. Cl.
CPC ............. *A61B 5/291* (2021.01); *A61B 5/168* (2013.01); *A61B 5/316* (2021.01); *A61B 5/377* (2021.01); *G06N 20/00* (2019.01); *A61B 5/162* (2013.01); *A61B 5/30* (2021.01); *A61B 5/7267* (2013.01); *G06N 3/08* (2013.01)

(58) Field of Classification Search
None
See application file for complete search history.

(56) References Cited

U.S. PATENT DOCUMENTS 5,807,246 A * 9/1998 Sakaguchi ............... G09G 3/14
  600/310
6,223,074 B1   4/2001 Granger
(Continued)

FOREIGN PATENT DOCUMENTS

EP    2408359    1/2012

OTHER PUBLICATIONS

Balconi et al. The Relationship Between Coma Near Coma, Disability Ratings, and Event-Related Potentials in Patients with Disorders of Consciousness: A Semantic Association Task. Appl Psychophysiol Biofeedback (2015) 40:327-337. (Year: 2015).*

(Continued)

*Primary Examiner* — Etsub D Berhanu
(74) *Attorney, Agent, or Firm* — Norton Rose Fulbright Canada LLP

(57) ABSTRACT

An improved system for assessing cognitive function is described that uses tracked electrical activity of the brain of the individuals in response to a specific sequence of stimuli in generating data sets, which, for example, can be encapsulated as a data structure. The data sets can include tracked specific response types, at different times and amplitudes, including, but not limited to, event related potential signal components. Brainwave features including, event related potentials, are tracked in relation to both pre-attentive brain responses and consciously controlled attention responses.

18 Claims, 22 Drawing Sheets

(51) Int. Cl.
    *A61B 5/00*           (2006.01)
    *A61B 5/30*           (2021.01)

(56) References Cited

U.S. PATENT DOCUMENTS

| | | |
|---|---|---|
| 6,280,198 B1 | 8/2001 | Calhoun |
| 6,434,419 B1 | 8/2002 | Gevins |
| 6,993,381 B2 | 1/2006 | Connolly |
| 7,454,243 B2 | 11/2008 | Silberstein |
| 8,473,043 B1 | 6/2013 | Modarres |
| 2003/0015384 A1 | 8/2003 | Kilborn |
| 2010/0094155 A1* | 4/2010 | Prichep .............. A61B 5/04845 600/544 |
| 2013/0028179 A1 | 1/2013 | Sedlacek et al. |
| 2013/0355791 | 2/2013 | Le et al. |
| 2013/0245422 A1* | 9/2013 | D'arcy ............... A61B 5/04012 600/409 |
| 2014/0012876 A1 | 1/2014 | Beskrovny et al. |
| 2014/0032390 A1 | 1/2014 | Glinberg et al. |
| 2014/0052016 A1 | 2/2014 | Cheng |
| 2015/0003886 A1 | 2/2015 | Simon et al. |
| 2017/0316707 A1 | 11/2017 | Lawrenson et al. |

OTHER PUBLICATIONS

International Search Report and Written Opinion issued in International Application No. PCT/CA2019/050982, dated Oct. 18, 2019.

\* cited by examiner

```
                                    1200

┌─────────────────────────────────────────────────────────────────────────┐
│ PRESENT A REPEATED AUDITORY TONE OR VISUAL IMAGE PRESENTATION TO THE    │
│ PATIENT, AND TRACK N1 AND P2 RESPONSES                                  │
│                                  1202                                   │
└─────────────────────────────────────────────────────────────────────────┘
                                    ▼
┌─────────────────────────────────────────────────────────────────────────┐
│ PRESENT ONE OR MORE AUDITORY OR VISUAL PHRASES EACH INCLUDING ONE OR    │
│ MORE NONSENSICAL, OR OTHERWISE INACCURATE OR UNEXPECTED PORTIONS OF A   │
│ SENTENCE, TRACK N400 RESPONSES                                          │
│                                  1204                                   │
└─────────────────────────────────────────────────────────────────────────┘
                                    ▼
┌─────────────────────────────────────────────────────────────────────────┐
│ PRESENT ONE OR MORE INCONGRUOUS, UNEXPECTED OR OTHERWISE SURPRISING     │
│ WORDS OR SENTENCES WITHIN A LANGUAGE CONTEXT, TRACK N400 RESPONSES      │
│                                  1206                                   │
└─────────────────────────────────────────────────────────────────────────┘
                                    ▼
┌─────────────────────────────────────────────────────────────────────────┐
│ PRESENT REPEATED TONES OR VISUALS INTERMIXED WITH DEVIANT TONES OR      │
│ VISUALS WHILE PRESENTED IN CONCERT WITH A CONSTANT TONE OR VISUAL,      │
│ TRACK MMN RESPONSES                                                     │
│                                  1208                                   │
└─────────────────────────────────────────────────────────────────────────┘
                                    ▼
┌─────────────────────────────────────────────────────────────────────────┐
│ PRESENT REPEATED TONES OR VISUALS INTERMIXED WITH DEVIANT TONES OR      │
│ VISUALS, TRACK P3A RESPONSES                                            │
│                                  1210                                   │
└─────────────────────────────────────────────────────────────────────────┘
                                    ▼
┌─────────────────────────────────────────────────────────────────────────┐
│ PRESENT REPEATED TONES OR VISUALS INTERMIXED WITH DEVIANT TONES OR      │
│ VISUALS WHILE THE PATIENT HAS BEEN INSTRUCTED TO ACTIVELY RECOGNIZE OR  │
│ RESPOND TO THE DEVIANT TONES OR VISUALS, TRACK P3B RESPONSES            │
│                                  1212                                   │
└─────────────────────────────────────────────────────────────────────────┘
                                    ▼
┌─────────────────────────────────────────────────────────────────────────┐
│ PRESENT COMPLEX VISUAL OR AUDITORY PATTERN STIMULI, AT LEAST ONE OF     │
│ WHICH ARE REPEATED THROUGHOUT THE SEQUENCE WHILE THE PATIENT HAS BEEN   │
│ INSTRUCTED TO ACTIVELY RECOGNIZE OR RESPOND TO THE REPEATED VISUALS OR  │
│ AUDITORY TONES OR PATTERNS,                                             │
│ TRACK P3B RESPONSES                                                     │
│                                  1214                                   │
└─────────────────────────────────────────────────────────────────────────┘
                                    ▼
┌─────────────────────────────────────────────────────────────────────────┐
│ PRESENT COMPLEX VISUAL OR AUDITORY PATTERN STIMULI, AT LEAST ONE OF     │
│ WHICH ARE REPEATED THROUGHOUT THE SEQUENCE WHILE THE PATIENT HAS BEEN   │
│ INSTRUCTED TO ACTIVELY IGNORE SPECIFIC VISUALS OR AUDITORY TONES OR     │
│ PATTERNS, AND RECOGNIZE OR RESPOND TO ALTERNATE REPEATED VISUALS OR     │
│ AUDITORY TONES OR PATTERNS,                                             │
│ TRACK N2B RESPONSES                                                     │
│                                  1216                                   │
└─────────────────────────────────────────────────────────────────────────┘
```

FIG. 12

SYSTEMS AND METHODS FOR COGNITIVE HEALTH ASSESSMENT

CROSS REFERENCE

This application is a non-provisional of, and claims all benefit, including priority to, U.S. Application No. 62/698,424, entitled "SYSTEMS AND METHODS FOR COGNITIVE HEALTH ASSESSMENT", filed on 2018 Jul. 16, incorporated herein by reference in its entirety.

FIELD

Embodiments described herein relate to systems, methods, and computer-readable media for assessing cognitive function in concussions and acquired brain injuries. More specifically, embodiments relate to computer-implemented devices, and apparatuses that are configured to execute, facilitate or support cognitive health assessments using technical approaches for monitoring electrical activity of the brain of an individual.

INTRODUCTION

Cognitive health assessments are useful in rehabilitation, diagnostics, prognostics, and assessing severity of neurocognitive issues that may, for example, arise following a concussion or an acquired brain injury.

Cognitive health assessments are difficult as cognitive function is challenging to measure. The most relevant metric for assessing and diagnosing the consequences of a concussion and acquired brain injury is cognitive function—how a brain responds to stimuli.

Increased challenges arise in relation to individuals who appear to be unresponsive (e.g., those who have severe brain damage), and are unable to provide meaningful responses to stimuli.

Where individuals are concussed or potentially concussed, there may be increased worry associated with a visit to a practitioner. An additional challenge is that the visit to the practitioner skews readings on subjective examinations, such as White Coat Syndrome.

SUMMARY

Improved approaches are described herein in relation to cognitive function to determine brain health, specifically applicable to concussion, comatose/unresponsive individuals, and acquired brain injury. Further applications include mental competency assessments, elderly competency assessments, neurodevelopmental disorder competency assessments, measuring drug effects on brain function, and general brain health tracking. Some approaches described herein are especially helpful for seemingly unresponsive individuals as indicators may establish that such individuals may potentially have cognitive function that was not recognized otherwise.

An improved system for assessing cognitive function is described that uses tracked electrical activity of the brain of the individuals in response to a specific sequence of stimuli in generating data sets, which, for example, can be encapsulated as a data structure. The data sets can include tracked specific response types, at different times and amplitudes, including, but not limited to, event related potential (ERP) signal components. Brainwave features including ERPs are tracked in relation to both pre-attentive brain responses and consciously controlled attention responses. The approach uses tracked electrical activity of the brain of the individuals (e.g., during rest or in response to a specific sequence of stimuli) in generating data sets, which, for example, can be encapsulated as a data structure, obtained from a sensory device coupled (e.g., attached) to the head of an individual. The data sets can include tracked specific response types, at different times and amplitudes, tracking signal strengths and latencies.

A computing device is utilized to generate, present (e.g., render on a screen, control actuation of a scent mechanism, play a sound on a speaker) a sequence of stimuli and the data sets are retrieved in accordance with both rest and event-related potentials as the sequence of stimuli are controlled to be presented by the computing device. Stimuli can include regular stimuli, and generated stimuli that is specifically adapted to be dissonant, incongruous, unexpected, surprising, or deviant (e.g., 2400 tones can be selected, for example, with 82% standard tones (at around 50 ms, 1000 Hz, 80 dB), and three types of deviant tones at 6% of the population each). Deviants, for example, can include duration deviants (e.g., 125 ms), frequency deviants (e.g., 1200 Hz), and intensity deviants (e.g., 90 dB SPL).

The generated stimuli and the regular stimuli are presented such that the order in which they are presented and the tracking thereof of electrical signals in the brains are relevant, in some embodiments.

The tracking of different electrical signals may location-based, in some embodiments for example, dividing the scalp into multiple regions of interest with statistical analyses being conducted in different scalp sectors, tracking electrical signal amplitude and latency. Specific event potentials are tracked in response to specific types of rest, stimuli, and modified stimuli, in accordance with a process for cognitive health assessments. The specific event potentials can include windows for detecting peak amplitudes.

As described in various embodiments, specific improved processes are used in combination with technical processing circuitry and sensors to generate data outputs that can be used to control graphical user interfaces, append information into health record data structures, or modify the functioning of medical devices (e.g., modifying thresholds or polling frequencies). The processes are useful in respect of providing a technical approach for investigating individuals who may have latent concussion symptoms that are otherwise hard to detect, or individuals who appear to be vegetative, comatose, or otherwise unresponsive.

The data sets can be used for generating data outputs that can be provided to downstream medical devices or systems for generating notifications, modifying treatment parameters (e.g., such as a polling rate or modifying notification thresholds), among others. In some embodiments, the outputs are utilized to update electronic health records, such as incorporating cognitive health assessment data into a patient's records so that it can be retrieved by a primary care practitioner.

Where electronic health records are appended with cognitive assessment details, medical devices can be automatically operated with modified parameters to, for example, increase machine vigilance of the individual (e.g., this comatose person may actually be responsive). Similarly, health records for individuals who are potentially concussed may be automatically processed to cause the population of additional follow up tests and diagnostics.

For example, a comatose or unresponsive patient may have a flag variable toggled such that the primary care practitioner knows that the data indicates that the individual may actually have cognitive function. Similarly, for a potentially concussed patient, the flag variable could indicate that the patient likely requires additional monitoring or treatment intervention.

The cognitive health assessment data, in some embodiments, is transformed into inputs that can be used to generate graphical user interfaces that include information that is adapted for display on a display screen or on a mobile device, for example, with interactive visual elements. A graphical user interface can include visual interactive or visual interface elements/controls which show electrical signal components tracked against population-level details, which can be changed from numerical representations into percentile value scales based against, demographically selected control groups. These percentile value scales, in some embodiments are factored into the size and shape of the graphical elements being rendered on the screen such that a user or a practitioner is able to visually understand the distinctions thereof.

In some embodiments, the processed data and/or the generated graphical user interface are appended into the electronic health record, such that a practitioner is able to quickly view the results when considering the type of care and therapy to provide to the individual.

Where individuals may report symptoms of a concussion have resolved, neurological function (brain function) consequences may still be present. Existing methods of assessment (neuroimaging, behavioural assessments) cannot objectively detect these deficits of brain function. Returning to activity/play while functional deficits are still present can be dangerous to the individuals and their community's safety (for example, ability to operate a motor-vehicle safely).

Current approaches of assessment for concussion and acquired brain injury rely heavily on subjective methods of assessment. Reliable, objective data to make an accurate diagnosis and target customized rehabilitation is required and not yet integrated as standard medical practice.

The current standard of assessment for concussion and acquired brain injuries (ABIs) is one or a combination of behavioural or neuropsychological tests, CTs or MRI scans. This gold standard is missing the most relevant metric for assessing concussion and ABIs—objective measurements of brain function. Clinicians today are forced to make decisions on patient treatment based on incomplete and often irrelevant information for the condition which means patients are not getting the right treatment fast enough, if at all.

Technical solutions are described herein, in the form of physical assessment devices, tools, methods, processes, and computer-readable media storing machine readable instructions, which when executed by one or more processors, perform steps of a method. In particular, a technical approach is utilized by a computer system that is configured to interoperate with or incorporate brain-sensing devices as well as stimulus presentment devices (e.g., auditory stimulus, visual stimulus, as well as deviant versions thereof).

Accordingly, a system is described that is adapted for performing cognitive health assessments (CHAs) that include innovative approaches of concussion and ABI assessment to provide functional data that is a direct measurement of brain function by using electroencephalography to measure EEG data and event related potentials (ERPs).

The approach for performing CHAs compares ERP/EEG data to existing methods of assessment (behavioural (always), neuro-imaging (when available)) to verify or dispute the finding and how they are relevant to the patient's functional consequences resulting from a concussion or acquired brain injury.

In some embodiments, the tool is a standalone, special purpose machine that is adapted for use in a clinical setting. The special purpose machine may have specialized software and hardware, such as optimized integrated circuits or field programmable gate arrays. For example, the tool may be provided on a medical cart, coupled to a patient (e.g., following a concussion or a coma inducing incident), and the CHAs are measured as stimuli are presented (e.g., sound tones, vibrations, visual stimuli, olfactory stimuli), or between when stimuli are presented. These stimuli are presented even to patients who are otherwise unresponsive (individuals with locked in syndrome, etc.). Locked in syndrome is a medical condition whereby a patient is aware but may not be able, or has a limited ability to move or communicate.

Neuroscientific approaches are utilized in establishing the proposed approaches of various embodiments herein in respect of concussion and acquired brain injuries, and the systems have been developed based on scientifically validated approaches of the Applicants. An objective, sensory-based assessment tool is described herein, automatically controlling stimulus presentation and response tracking to generate a comprehensive patient report on their brain function shown through performance data for the purpose of clinical intervention by a clinical specialist.

A benefit for patients in a clinical setting is that the objective, sensory-based assessment tool does not suffer from the "noise" caused by a patient's emotions and feelings (e.g., fears of a clinical environment and worry can, for other tests, lead to a false positive reading, for example, due to White Coat Syndrome, among others). A benefit for the clinician and/or other stakeholders involved in the patient's case is the ability to identify patients who are malingering. Other "noise" that may be present in subjective tests in relation to jaw clenching, and blinking, may also be accounted for.

In accordance with an aspect, a computing system for cognitive health assessments is provided, the computing device including at least one processor and computer readable memory.

The computing system includes a sensor apparatus connected to one or more electrodes coupled to a patient's head, the one or more electrodes recording brainwave data of the patient, and a stimulus presentation mechanism coupled to one or more sensory output devices (in some embodiments, coupled to the computing system or part of the system), the stimulus presentation mechanism generating a series of programmed stimuli to the patient while the sensor apparatus records the brainwave data of the patient as the patient receives the series of programmed stimuli.

These electrodes and the stimulus presentation mechanism operate in concert with one another, based on an automated test protocol. Time-coded data sets are extracted, and brainwave data is correlated with event-based timing. The brainwave (i.e., EEG) data may include, for example, MMN responses, P300 responses, N400 responses, P3a, P3b, N1, among others. Not all embodiments are limited and the above are provided as illustrative examples.

A waveform feature extractor processing engine is provided that is configured to process the brainwave data of the patient to extract one or more waveform features, the one or more waveform features including for example, one or more P300 responses and/or one or more N400 responses.

A cognitive health assessment controller is configured to record, using the sensor apparatus, a first portion of brainwave data of the patient during a first resting period during which no stimuli are being presented to the patient, control the stimulus presentation mechanism to present a repeated auditory tone (or, in alternate embodiments, visual stimulus or a combination thereof) to the patient; control the stimulus presentation mechanism to present the repeated auditory tone intermixed with deviant tones (e.g., two or more different sets of tones), and control the waveform feature extractor to track differences in the one or more P300 responses recorded in the one or more waveform features during the presentation of the repeated auditory tone to the patient and during the presentation of the repeated auditory tone intermixed with the periodic deviant tones.

Deviant tones may include, for example, random words, recognizable sounds, among others. Deviant sounds can include unfamiliar novel sounds (e.g., dog barks, doorbells), non-salient words (e.g., "NSOW"). Visual stimulus may include repeated visual stimuli followed by deviant visual stimuli. A combination thereof may include deviant tones relative to a visual stimulus, or vice versa. Similarly, vibro-tactile stimuli are also possible, by way of mechanical vibrations (e.g., by way of a mechanical instrument coupled to the body of the patient configured such that individuals are able to detect or respond to stimuli using a sense of touch. Vibrations may be sensed through resonant materials, etc.).

In another aspect, the cognitive health assessment controller is further configured to: control the stimuli presentation mechanism to present the repeated auditory tone intermixed with periodic deviant tones, that are distinct from each other, and track differences in the one or more P300 and MMN responses recorded in the one or more waveform features during the presentation of the repeated auditory tone presentation intermixed with the deviant tones and during the presentation of the repeated auditory tone intermixed with the deviant tones.

In another aspect, the cognitive health assessment controller is further configured to: control the stimuli presentation mechanism to present one or more auditory phrases each including one or more nonsensical portions to the patient; and control the waveform feature extractor to track the one or more N400 responses recorded in the one or more waveform features during or proximate to the presentation of the one or more incongruous, nonsensical or unexpected portions.

In another aspect, the processor is configured to augment the brainwave data with time-codes contemporaneous or near contemporaneously with presentation of the series of programmed stimuli.

In another aspect, the series of programmed stimuli further include one or more outlier tones in addition to the repeated auditory tone presentation (e.g., different presentation depending on the paradigm of the test, for example, for an MMN test for involuntary attention for healthy human beings, the individual is watching a video and the test examines the involuntary recognition of the deviant tone while they're watching the show, and in another example, if investigating a P300 response, the patient is instructed to pay attention to the tones, and press a button each time the patient hears the deviant tone.

In another aspect, the system includes a video recording device adapted to obtain video data of the patient as the patient undergoing the test.

In another aspect, the system delivers a sequence of visual stimuli and the patient is instructed to press a button if a stimulus is repeated to track one or more N2b responses.

In another aspect, the patient is in an unresponsive state and the sensor apparatus is configured to record the brainwave data of the patient during one or more additional rest periods where the patient is not receiving the programmed stimuli.

In another aspect, the brainwave data of the patient during one or more additional rest periods, where the patient is not receiving the programmed stimuli, is combined with the brainwave data of the patient recorded proximate in time to the presentation of the programmed stimuli.

In another aspect, the system further includes a display controller coupled to a display, the display controller configured to render a brain assessment interface including at least a representative mapping of a brain of the patient indicative of one or more functions of the brain are activated proximate to or responsive to the presentation of the series of programmed stimuli. The assessment interface is configured to provide a decision support interface, capable of aiding practitioners in making informed decisions in respect of a patient's prognosis or treatment. Specifically rendered displays are generated responsive to sensory readings.

In another aspect, the system further includes a display controller coupled to a display, the display controller configured to render a brain assessment interface including at least a representative mapping of a brain of the patient indicative of one or more functions of the brain are activated during one or more rest periods between the presentation of the series of programmed stimuli.

The brain assessment interface renders diagrams with superimposed waveforms over one or more reference diagrams, indicative of a severity of injury. Comparison values are provided indicating locations of waveform peaks, comparisons against similar demographics or control groups, among others. For example, "heat maps" may be generated where deviations from a demographic norm are shown, whereby the heat maps indicate severity and are directed to the brain's ability to function certain tasks as opposed to showing physical damage (e.g., not "left frontal lobe") but rather, showing long/short term memory injury mapped to a functional category.

In another aspect, the brain assessment interface renders one or more visual indicators identifying at least one of a severity of injury, the region where the functional injury is located within the brain, and whether the injury is affecting normal brain function. The visual indicators may be rendered over a rendered head or brain or on a scaled graph.

In another aspect, the system generates one or more statistical analyses in the form of one or more reports.

In another aspect, a method for generating data sets representative of potential cognitive activity of a patient is provided, the method including: recording, using a sensor apparatus connected to one or more electrodes coupled to the patient's head, the one or more electrodes recording brainwave (EEG) data of the patient in respect of a brain of the patient, a portion of brainwave data of the patient during a first resting period during which no stimulus is being presented to the patient; controlling a stimulus presentation mechanism to present a repeated auditory tone or visual image presentation to the patient; tracking, on a processor configured for monitoring data received from the sensor apparatus: the one or more N1 and P2 responses to auditory tones or visual images to measure the brain's processing of auditory stimuli or N1 and P2 responses to visual stimuli to measure the brain's processing of the visual stimuli; controlling the stimulus presentation mechanism to present one or more auditory or visual phrases each including one or more nonsensical, or otherwise inaccurate or unexpected portions of a sentence to the patient; tracking, by the processor: the one or more N400 responses recorded in one or more waveform features during or proximate to the presentation of the one or more nonsensical portions of the sentence to measure the brain's ability to process word and phrase meanings, sentence grammar and discourse; controlling the stimulus presentation mechanism to present one or more incongruous, unexpected or otherwise surprising words or sentences within a language context; tracking, by the processor: the one or more N400 responses recorded in one or more waveform features during or proximate to the presentation of the one or more incongruous, unexpected or otherwise surprising words or sentence pairings to track the brain's ability to process word and phrase meanings, and vocabulary recognition; controlling the stimulus presentation mechanism to present repeated tones or visuals intermixed with deviant tones or visuals while presented in concert with a constant tone or visual; and tracking, by the processor: the one or more MMN responses recorded in one or more waveform features during or proximate to the presentation of the one or more deviant tones or visuals to track the brain's ability to respond to environmental changes that are not actively attended; controlling the stimulus presentation mechanism to present repeated tones or visuals intermixed with deviant tones or visuals; tracking, by the processor: the one or more P3a responses recorded in one or more waveform features during or proximate to the presentation of the one or more deviant tones or visuals to track the brain's ability to respond to stimulus deviance; controlling the stimulus presentation mechanism to present repeated tones or visuals intermixed with deviant tones or visuals while the patient has been instructed to actively recognize or respond to the deviant tones or visuals; tracking, by the processor: the one or more P3b responses recorded in the one or more waveform features during or proximate to the presentation of the one or more deviant tones or visuals to track the brain's ability to focus one's attention on a task; controlling the stimulus presentation mechanism to present complex visual or auditory pattern stimuli, at least one of which are repeated throughout the sequence while the patient has been instructed to actively recognize or respond to the repeated visuals or auditory tones or patterns; tracking, by the processor: the one or more P3b responses recorded in one or more waveform features during or proximate to the presentation of the one or more repeated tones or visuals or patterns to track the brain's ability to temporarily hold information available for processing; controlling the stimulus presentation mechanism to present complex visual or auditory pattern stimuli, some of which are repeated throughout the sequence while the patient has been instructed to actively ignore the specific visuals or auditory tones or patterns, and recognize or respond to the alternate repeated visuals or auditory tones or patterns; tracking, by the processor: the one or more N2b responses recorded in one or more waveform features during or proximate to the presentation of one or more repeated tones or visuals and reaction to one or more repeated tones or visuals to track the brain's ability to work through complex processes to enable complex behaviour; differences in the N1, P2, N400, MMN, P300 (P3a/P3b), N2b responses recorded in the one or more waveform features during the presentation of the repeated auditory tone or visual image presentation to the patient and during the presentation of the repeated auditory tone or visual image intermixed with the deviants; the one or more P3b responses recorded in one or more waveform features in response to complex visual pattern stimuli, some of which are repeated throughout the sequence; and generating a data set based on the extracted waveform features, the data set including data fields corresponding to at least one of an automatic attention metric based at least on the differences in the one or more MMN responses, a reactive attention metric based at least on the differences in the one or more P3a responses, a concentration metric the differences in the one or more P3b responses, a working memory metric based at least the differences in the one or more P3a responses, or an executive function metric based at least on the differences in the one or more N2b responses.

In another aspect, the generated data set is appended to an electronic health record data structure associated with the patient.

In another aspect, a normalized and transformed data set is generated and appended to an electronic health record data structure associated with the patient.

In another aspect, the generated data set is transmitted to a medical monitoring apparatus coupled to the patient, and wherein the medical monitoring apparatus modifies one or more or operating parameters responsive to the data fields, the one or more operating parameters including at least a polling frequency of the medical monitoring apparatus.

In another aspect, the generated data set is transmitted to a medical monitoring apparatus coupled to the patient; and the medical monitoring apparatus, responsive to a determination that the data fields indicating that one or more of the automatic attention metric, the reactive attention metric, the concentration metric, the working memory metric, or the executive function metric are greater than a pre-defined threshold, is configured to generate an alert or notification.

In another aspect, the processor is a plurality of distributed computing resources that operate in concert to process the brainwave data of the patient.

In another aspect, the patient is elderly, disabled, diagnosed with a potential concussion or acquired brain injuries, is in an unresponsive state or is comatose.

In another aspect, the patient is an individual diagnosed with a potential concussion or acquired brain injuries, wherein the differences relating to one or more MMN responses, the one or more N2b responses or the one or more P3b responses are used to indicate a level of severity of the potential concussion or acquired brain injuries.

In another aspect, the patient is in an unresponsive state and the sensor apparatus is configured to record the EEG data during one or more resting periods where the patient is not receiving the series of the programmed stimuli.

In another aspect, the patient is in comatose and the sensor apparatus is configured to record the EEG data during one or more resting periods where the patient is not receiving the series of the programmed stimuli.

In another aspect, system is used in relation to general brain health tracking.

In this respect, before explaining at least one embodiment in detail, it is to be understood that claimed embodiments is not limited in its application to the details of construction and to the arrangements of the components set forth in the following description or illustrated in the drawings. Other embodiments are possible and carried out in various ways. Also, it is to be understood that the phraseology and terminology employed herein are for the purpose of description and should not be regarded as limiting.

BRIEF DESCRIPTION OF DRAWINGS

Embodiments will now be described, by way of example only, with reference to the attached figures, wherein:

FIG. 7A shows auditory N1/P2, MMN waveforms, FIG. 7B shows visual N1/P2, P3b waveforms, FIG. 7C shows N2b, P3a, P3b waveforms, FIG. 7D shows a N4 waveform.

FIGS. 8A-8C illustrates topographical mapping generated throughout waveform data collection. Areas of the brain 'light up' at the time of an ERP response. Although one may see irregular responses in waveforms, one may not see irregularities on the topographical maps or vice versa. Therefore, topographical maps confirm the elicitation of an ERP. FIGS. 8A-C shows grand-averaged P300 protocol waveforms and their respective scalp distributions recorded at Cz, evoked by target stimuli, for each group (Controls Left, Concussed person, Right). FIG. 8A: N1, N2b, P3a, and P3b components evoked in the Frequency condition. (B) FIG. 8B: N1, N2b, P3a, and P3b components evoked in the Duration condition. (C) FIG. 8C: N1, N2b, P3a, and P3b components evoked in the Intensity condition.

FIG. 12 is a method diagram of an example process, according to some embodiments.

Figure 1A:
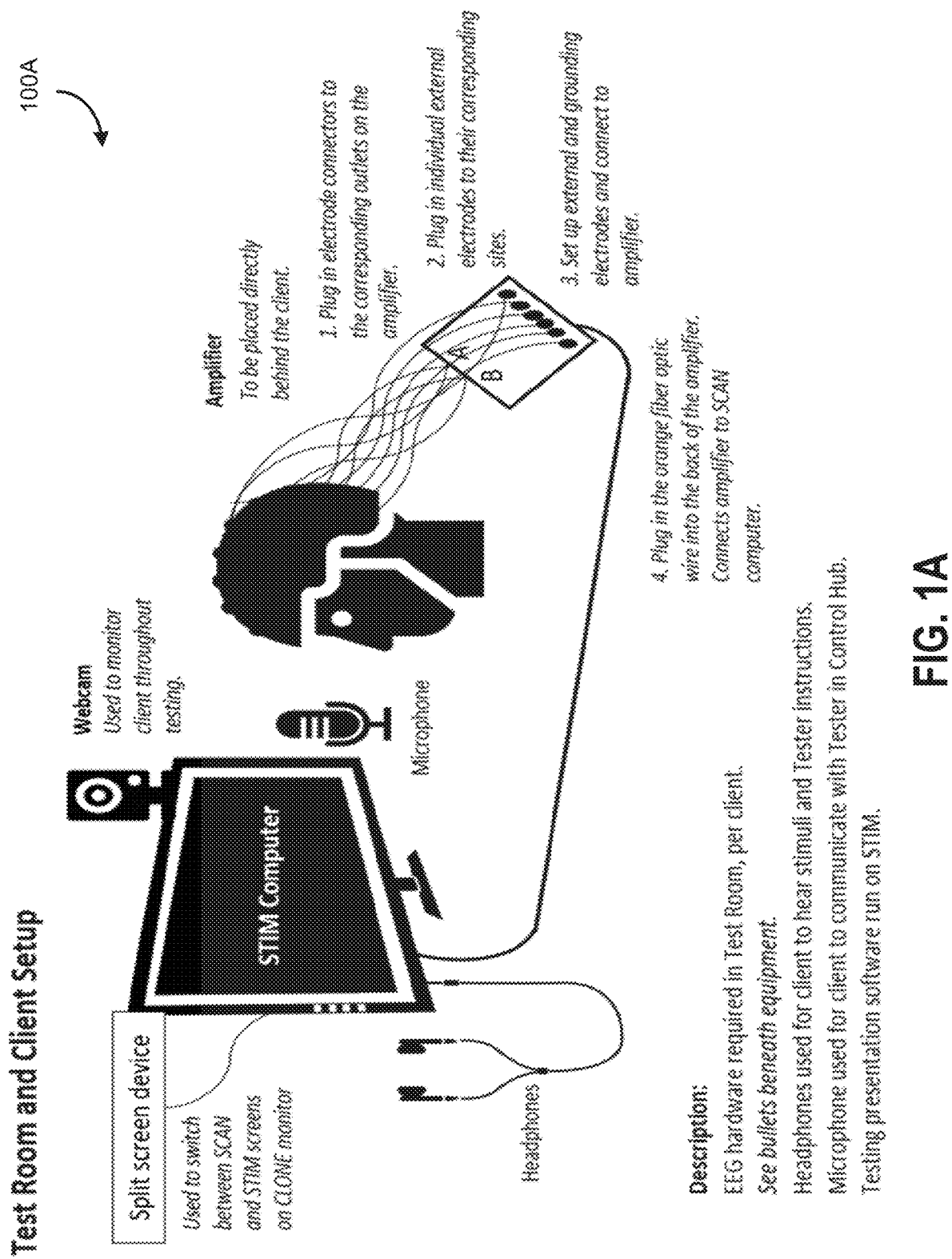
FIG. 1A is a schematic diagram depicting a physical apparatus for implementing a cognitive health assessment, according to some embodiments.

In the drawings, embodiments are illustrated by way of example. It is to be expressly understood that the description and drawings are only for the purpose of illustration and as an aid to understanding, and are not intended as a definition of the limits of the claimed embodiments.

DETAILED DESCRIPTION

The current standard of assessment for concussion and acquired brain injuries (ABIs) is one or a combination of behavioural or neuropsychological tests, CTs or MRI scans. This gold standard is missing the most relevant metric for assessing concussions and ABIs—objective measurements of brain function. Clinicians are forced to make decisions on patient treatment based on incomplete and often irrelevant information for the condition which means patients are not getting the right treatment fast enough, if at all.

An industry-first objective concussion and acquired brain injury assessment system and corresponding methods and computer-readable media are described herein. The approach delivers quantitative insights on patients' brain function that inform, accelerate, and track recovery with unprecedented precision. Applicants note that there is no other concussion and acquired brain injury assessment clinically available that provides legitimate measurement of brain function to objectively and specifically inform cognitive rehabilitation in all core functions: auditory processing, visual processing, information processing, automatic attention, reactive attention, concentration, memory, language comprehension and executive function.

An improved system is provided that includes, in some embodiments, brain sensing devices (e.g., electrodes), stimuli presentment mechanisms (e.g., display screens, vibration motors, speakers, olfactory release devices), and computer instruction sets for controlling measurement and stimuli presentment is described. The stimuli presentment is controlled to include various repeated, transformed and/or deviant versions of stimuli, and automatic early attentional brain mechanisms and/or consciously controlled attention mechanisms are triggered by such repeated, transformed and/or deviant versions of stimuli. The tracked data, in some embodiments, is processed to extract one or more data sets, which can be used for modifying device operational parameters, updating electronic health records, or as inputs for controlling rendering of a graphical user interface, according to various embodiments.

Traditional EEG is used in clinical practice, and quantitative EEG (qEEG) is becoming more common, to assess seizures and sleep disorders. In some cases, they may also be used to help assess severe brain injuries.

EEG testing available in most clinics and hospitals is capable of capturing ongoing brain-signals and oscillations passively (e.g., alpha and beta brain waves), and is commonly known as "resting state". Clinicians typically 'read' traditional EEG scans free-form. qEEG is an improvement on traditional EEG in the way it analyses a patient's data, statistically comparing their results to healthy controls.

The detection of abnormal brain function as a result of a concussion or acquired brain injury using resting state testing methods with traditional EEG or qEEG is only possible within the first 72 hours post-injury. Otherwise, these methods cannot find useful information regarding a concussion or acquired brain injury because the perturbation of resting brain waves return to normal after 72 hours.

Cognitive health assessments as described herein use EEG equipment, and the use of these systems expand the range of measurable brain activity by enabling direct measurement of the brain's responses to stimulation and cognitive tasks. The approach described includes specific computer-controlled sequences and controlled measurements thereof. In some embodiments described herein, enhanced EEG equipment is utilized that is research grade, and capable of expanding the range of measurable brain activity.

The embodiments described herein tracks a patient's active responses to a range of tasks and stimuli instead of only at a resting state. The system can include stimuli generating/presenting mechanisms which are selectively actuated in accordance with a specific process or sequence of cognitive function measurements through brain electrical impulse sensing apparatuses. Event related potentials (ERP) measures are tracked to assess different levels of conscious processing and presence of signs of a conscious state predictive of subsequent emergence or potential undiagnosed injury.

Stimuli can include regular stimuli, and generated stimuli that is specifically adapted to be dissonant, incongruous, unexpected, surprising, or deviant (e.g., 2400 tones can be selected, for example, with 82% standard tones (at around 50 ms, 1000 Hz, 80 dB), and three types of deviant tones at 6% of the population each). Deviants, for example, can include duration deviants (e.g., 125 ms), frequency deviants (e.g., 1200 Hz), and intensity deviants (e.g., 90 dB SPL).

This active engagement with stimuli throughout testing, which can be thought of as a stress-test or performance-test for the brain, is how the system is able to provide objective data on specific brain functions that require rehabilitation, instead of generalizing the higher-level brain function of a patient at resting state—to see if their brain function looks normal or injured.

Information on whether a brain is functioning normally or not is valuable in making an initial diagnosis within the first 72 hours post-injury, but does not allow clinicians to objectively inform targeted cognitive rehabilitation plans. Cognitive health assessments can be run at various times, whether an injury happened 2 days ago or 20 years ago, to quantify the functional issues and objectively inform a treatment path.

Further explaining the novel-ness of the approach disclosed as compared to traditional EEG, qEEG and other newer EEG based cognitive assessment tools, is in the combination of ERPs recorded, to be able to provide a fulsome report on each core area of cognitive function required to inform a complete and customized cognitive treatment plan, unique to each patient. Many newer EEG technologies rely on a single ERP (e.g., P300), or a combination of up to three (e.g., N1, P300, N400) to understand if a patient's brain function is abnormal as compared to healthy controls, indicating a concussion or brain injury is present.

However, these measurements alone cannot provide the level of insight required to create an objective, unique and customized treatment plan for patients. An improved system for assessment of brain injuries, actual, or potential, is disclosed in some embodiments.

The system is a computer implemented system that provides physical assessment devices, tools, methods, processes, and computer-readable media storing machine readable instructions, which when executed by one or more processors, perform steps of a method. The system is adapted for performing cognitive health assessments (CHAs) that include innovative approaches of concussion and ABI assessment to provide functional data that is a direct measurement of brain function activity by using EEG and measuring activity including: event related potentials (ERPs), power spectrum, connectivity, coherence, frequency following responses and related stimulus contexts.

The system, in alternate embodiments, is a software-as-a-service platform (SaaS) hosted on physical distributed resources that are accessible through communications networks. In a SaaS implementation, analyses may be conducted despite local unavailability of extensive computing resources. For example, a mobile hospital or a remote hospital or clinic would be able to conduct the tests on physical devices (e.g., a processor, stimulus effectors [e.g., speakers], data recorders, sensors) that are locally present. The information may then be transmitted to a distributed resource or implementation (e.g., a cloud of computing resources) for processing. Outputs from the system indicative of an analysis, or assessment are generated, and potentially provided back to the mobile/remote hospital or clinic. The SaaS platform may be configured to capture the raw bio-signal data and present a decision support interface that a practitioner can readily view and interact with in preparing a diagnosis.

For more severe ABIs, and even sometimes for a suspected concussion or mild traumatic brain injury, CT or MRI scans can be one of the first methods of assessment. These imaging scans are relevant for showing structural damage—fractures to the skull, lesions in brain tissue and brain bleeds. If the scans show structural damage, it can be indicative that functional damage also exists, but further examination is required to confirm this. It is possible for a patient to have structural damage but still be 'normal' in terms of function, and it is also possible for a patient to not show any signs of structural damage but have severe functional damage that would not be uncovered by these assessments—meaning that traditional neuroimaging risks missing the concussion or mild traumatic brain injury, or improperly assessing a more traumatic injury—potentially leading to a misdiagnosis for the patient.

In other approaches, those further assessments would be neuropsychological testing or behavioural testing as an attempt to measure functional damage, but their results remain subjective and require expert best judgement to diagnose. The tests described herein, in some embodiments, expand on industry standard neuropsychological assessments and are adapted to provide objective analyses of brain function.

The responses to neuropsychological and behavioural testing are more accurate through cognitive health assessments according to various embodiments because they turn subjective measurements (neuropsychological or behavioural test results on their own) into objective measurements (neuropsychological testing while measuring ERPs with EEG and related measures, and compared to behavioural tests, and neuroimaging results when available).

When a neuropsychologist or clinician using behavioural tests assess a patient, the reliance on behaviour alone leaves a margin for error based on the patient's engagement with the testing and the neuropsychologists/clinicians interpretation of the patient's answers.

With EEG being used to complete these measurements for actual electrophysiological brain responses, it is possible to obtain results that are not dependent on interpretation of information that is itself subjective and demonstrably, situationally, insensitive rather than objective. The results provide clinicians with objective data on brain function. This makes cognitive health assessments results more useful than classic neuropsychological or behavioural tests because it has removed the potential for human error. Brain responses cannot be manipulated in EEG testing, whereas with neuropsychological, or any behavioural tests, the patient can lessen or increase the measurement of their severity of injury based on how they respond to testing—be that manipulation intentional or not.

As noted herein, the brain responses measured can include obligatory sensory responses that can be used to assess, through the selective presentment of stimuli, objective evidence of brain function despite a patient not showing signs otherwise. Obligatory responses can be evoked by the selective presentment of stimuli, such as deviants, and dissonant sounds/images, and nonsensical lexical pairings, and the descriptions herein relate to mechanisms for tracking electrical brain impulses in respect of "pre-attentive cognitive processes". Accordingly, the signals tracked herein are obtained without requiring a subject's active involvement. In particular, the P300 and the MMN have a good correlation with coma awakening.

Seven examples of how the cognitive health assessments positively intervened/provided added value with a patient's concussion or acquired brain injury journey are as follows:

Concussion Example 1

Patient "A" scored highest on the behavioural assessment portion of the applicant's study comparing the largest dataset of living ex-pro football players to healthy controls to date that leveraged EEG to measure brain function. The study compared behavioural and neuropsychological assessment, to functional MRI and the EEG protocol of the cognitive health assessment. When Patient "A" scored the highest on the behavioural assessment, traditionally this would indicate he ranked as the "most damaged/injured" as a result of physical impact he incurred throughout his professional football career, indicating long-term cognitive damage.

However, the cognitive health assessment (which recorded his brain function as it pertained to: Auditory Processing (N1/P2), Visual Processing (N1/P2), Information Processing (all ERPs), Automatic Attention (MMN), Reactive Attention (P3a), Concentration (P3b), and Working Memory (P3b) in this case), provided objective data that proved Patient "A" was in fact experiencing no functional consequences from his time as a professional football player, and that his high score on the behavioural assessment portion of the study was due to his anxiety/paranoia about his condition following the growing prevalence of concussion issues surfacing in mainstream media. In other words, when he forgot why he walked into the kitchen at home it was simply forgetfulness, and not due to functional damage incurred during his professional football career.

Had Patient "A" not received the cognitive health assessment, he would not have received verification if his suspicions/high-scoring behavioural tests were accurate and if rehabilitation was required.

The cognitive health assessment provided objective evidence that demonstrated he was, in fact, cognitively healthy when compared to matched controls—a finding that was in contradiction to his subjective impressions. Patient "A" thus received confirmation that his self-reported symptoms were linked to psychological conditions due to fear of the unknown of how is career may have impacted his brain health. The objective confirmation of the health of his brain function provided mental relief and guided that if ongoing symptoms persisted his next steps in treatment could be appropriately tailored to his needs regarding his anxiety.

The MRI portion of the study supported the EEG data that this patient also had no structural damage, for example measured by diffusion tensor imaging measures. The patient was in fact the healthiest participant on both the EEG cognitive health assessment and MRI portions of the study.

Concussion Example 2

Patient "B" was struck by a car as a pedestrian. They lost consciousness at the scene and were diagnosed with a "moderate-to-severe" concussion at the hospital the next day as a result of their physical and behavioral examination. They went on to have two CT scans, an optometrist exam and a psychological assessment.

The CT scans both turned up negative and the optometrist exam was clear (indicating no concussion by the hospital's standard protocol, meaning the initial diagnosis was unclear.) The psychological assessment uncovered a history of mood disorder. Due to Patient "B"'s history of mood disorders, many of their symptoms the patient associated with the concussion incident were attributed to the pre-existing mood conditions.

This led to Patient "B" being treated with pharmaceutical intervention and counselling being prescribed as their treatment strategy. Patient "B"'s symptoms worsened, compounding pre-existing anxiety and depression. Patient "B" could not return to work and withdrew from socializing due to issues with concentrating, performing day-to-day tasks and following conversation.

Two years post-injury, Patient "B" was still suffering from symptoms not present prior to the injury and others compounded since the injury. Patient "B" sought out alternate treatment and as a result were enrolled in a pilot program performed by the applicants in partnership with a rehabilitation group. Patient "B"'s initial cognitive health assessment confirmed the patient suffered from cognitive dysfunction in Automatic Attention (MMN), Reactive Attention (P3a), Concentration and Working Memory (P3b)—all results showed "moderate deficiency" or "severe deficiency" as compared to healthy controls.

The rehabilitation group prepared a cognitive therapy plan based on the deficits indicated, and Patient "B" embarked on a 10 week rehabilitation plan with their occupational therapist. At the end of the treatment plan, Patient "B" was reassessed using the cognitive health assessment.

The follow-up report showed improvements in cognitive functioning in all of the areas previously identified as below a healthy norm. Automatic Attention, Reactive Attention and Memory results all fell within the healthy range and were recorded as "normal" compared to healthy controls, and Concentration performance was only slightly below, while still falling into the "moderate deficiency" category as compared to healthy controls.

Throughout Patient "B"'s experience with the cognitive health assessments and subsequent cognitive rehabilitation (which they would not have received without the cognitive health assessment), they also saw gradual improvements in their mood conditions due to the confirmation that cognitive deficits as a result of their injury were in fact present.

This confirmation allowed the patient to better understand their symptoms and provided them motivation with tangible goals and actions to act upon to better their mental and cognitive health. Patient "B" is continuing to work on strategies for Concentration, and has begun to re-engage socially, and returning to work on a part time basis.

The objective data provided by the cognitive health assessment allowed Patient "B"'s care team to take a multidisciplinary approach which lead to Patient "B" being more motivated and inspired to work on their recovery, knowing they would be able to quantify their improvements with the cognitive health assessment's objective results.

Concussion Example 3

Patient "C" is a unique case who was a part of the applicants' study on ex-pro football players as a healthy control. Patient "C" later was a party to a motor vehicle accident that lead to a diagnosis of a mild concussion. The diagnosis was given following a physical and behavioural examination at hospital.

A CT scan was run, and the results were negative. Patient "C" was monitored throughout the first four weeks of their concussion, but symptoms (including headache, dizziness, cognitive and physical fatigue, and tinnitus) persisted. After months of symptoms not resolving, Patient "C" sought out a cognitive health assessment. Patient "C" was tested for Auditory Processing (N1/P2), Visual Processing (N1/P2), Information Processing (all ERPs), Language Comprehension (N400), Automatic Attention (MMN), Reactive Attention (P3a), Concentration (P3b), Working Memory (P3b) and Executive Function (N2b/P3b). "Moderate deficiency" was identified for Automatic Attention, Reactive Attention, Working Memory and Executive Function. "Severe deficiency" was indicated for Concentration.

All of Patient "C"'s core cognitive functions were confirmed to have been affected by the motor vehicle accident. Patient "C" has enrolled in a 10 week rehabilitation plan to work on the deficits identified and will be reassessed mid-rehabilitation and post-rehabilitation to support their clinician's ability to medically clear the patient to return to regular activity—for them, meaning full-time work and recreational sports.

Both Patient "B" & "C" had struggled to manage their symptoms and lack of objective evidence when working with their employers on dealing with their injuries. The cognitive health assessments provided both objective evidence to the employers of the injury and informed them of which areas the patients were suffering in, allowing for accommodations to be strategically planned for as they worked through their recovery.

Both patient "B" and "C" qualified for motor-vehicle insurance coverage for their cognitive health assessments and subsequent treatment based on the objective information the cognitive health assessments provided, which they previously had not been deemed eligible for due to lack of evidence of the injury and its impact on the patients' lives.

The objective data provided in cognitive health assessment reports allow clinicians to pinpoint and address the root of the cognitive impairments a patient is dealing with, in addition to treating observable/reported symptoms and functional impairments. Knowing areas of cognitive deficit is essential for rehabilitation professionals to facilitate the patient's return to pre-accident functioning and improve their quality of life, as proven to have been the case in all of the concussion examples provided herein.

Concussion Example

Patients who show no physical damage according to MRI scans, score "healthy" on behavioural and neuroimaging assessments, but know there is "something wrong" i.e. they are concussed but have no other methods of assessment to consider to objectively confirm the injury.

Cognitive health assessments can detect functional consequences of concussion even when patients show no signs of concussion from today's gold standard of assessment. Function is the most relevant metric and not currently leveraged in an objective method in today's gold standard of concussion assessment.

ABI Example 1

Patient "D" was struck by a car while on a bike and thrown 30 meters. They were deemed catastrophically injured with no vitals on the scene. After being resuscitated by paramedics and operated on in hospital for 12 hours to stabilize their condition, Patient "D" was confirmed to have sustained severe brain and abdominal injuries and diagnosed as being in a vegetative state—now referred to as unresponsive wakefulness syndrome (UWS) (vegetative state).

After slipping in and out of a coma for 10 days, Patient "D" was transferred to a step-down clinic where they regained consciousness and were tested by the principal neurologist at the facility. The neurologist was unsure of the original diagnosis of vegetative state due to how the patient was responding to their testing.

The scores they most commonly relied on, the Coma Recovery Scale (CRS-R) and Glasgow Coma Scale (GCS) scores classified the patient as vegetative, but the neurologist was not convinced. The neurologist referred Patient "D" to the applicants to perform a cognitive health assessment to determine if brain function could be detected. The MMN (Automatic Attention), P300s (Reactive Attention, Concentration, Working Memory), and N400 (Language Comprehension) tests as described under the UWS protocol in FIG. 5A were run. The results confirmed not only was brain activity present, but responses were fairly strong, indicating that Patient "D" had the potential to respond to rehabilitation efforts by their care team.

The results of the cognitive health assessment that objectively supported the neurologist's belief that the patient was not in fact in a vegetative state, granted the patient the opportunity to be transferred to the acquired brain injury unit for rehabilitation. Without the objective results of the cognitive health assessment, the patient would not have been awarded the opportunity for treatment due to an absence of objective data to indicate they had the potential to be rehabilitated.

Post-injury, Patient "D" lives at home with their family, has regained healthy cognitive activity, has limited ability to communicate through speech but can communicate effectively with care providers and family, and exercises seven days a week to continue to build physical strength.

ABI Example 2

Patient "E" suffered from a gunshot wound to the head. Following extensive surgery to stabilize their condition, the patient was deemed vegetative and placed in palliative care. The family of Patient "E" believed the patient was inaccurately diagnosed, and was actually in a "locked-in" state—a condition in which a patient is aware but cannot move or communicate verbally due to complete paralysis of nearly all voluntary muscles in the body except for vertical eye movements and blinking.

After 2 years of little progress, the family was struggling with the decision to keep Patient "E" on life support, which lead to the family's request for a cognitive health assessment to provide them with objective data to assist their decision. The MMN (Automatic Attention), P300s (Reactive Attention, Concentration, Working Memory), and N400 (Language Comprehension) tests as described under the UWS protocol in FIG. 5A were run. The results demonstrated that despite significant brain injury, Patient "D" retained some cognitive functioning in Automatic Attention, Reactive Attention and Memory. Language Comprehension was not found present which was likely due to their lack of response in Visual Processing, due to the nature of how the test was administered with visual stimuli. Given the identified complications with sight, follow-up to determine Language Comprehension through auditory stimuli was recommended.

As a result of Patient "E"'s cognitive health assessment, their care team and family began engaging with Patient "E" in ways they knew would be more effective given their abilities, e.g., communicating verbally instead of relying on recognition through sight. Therapeutic intervention is being pursued based on the confirmation of conscious awareness in Patient "E".

ABI Example

Unresponsive wakefulness syndrome (UWS, previously referred to as vegetative state) and coma patients were traditionally impossible to assess to determine their outcome potential due to their inability to engage with a healthcare professional's assessment.

Historically, rehabilitation facilities for this patient population have relied heavily on patients' progress through trial and error rehabilitation methods. With the cognitive health assessment reports, the rehabilitation providers are able to assess a patient's level of consciousness to predict their outcome and identify their "potential outcome potential", thus assisting families of patients who need to make a decision on proceeding with treatment, and provide direction for those who show potential based on their results.

For unresponsive wakefulness syndrome (UWS) (vegetative state) or coma patients specifically, the cognitive health assessment reports help the patients' families understand, with the objective data, what levels of consciousness the patient has, facilitating a confident decision in their next steps to pursue treatment, or take the patient off of life support. When cognition is identified meaning the patient has rehab potential, the reliable, quantitative data has helped facilitate the patients' families securing funding for their treatment.

A patient in an unresponsive wakefulness syndrome (UWS) (vegetative state) or within a coma may have some conscious awareness but be unable to respond due to sensory or perceptual impairments, aphasia, motor impairments, subclinical seizure activity, pain, fluctuating arousal, fatigue, and a range of other problems. With conventional assessment tools such a patient would receive an inaccurate diagnosis of UWS (VS). This scenario is far from uncommon.

Without the cognitive health assessment reports, the healthcare providers and families need to make decisions for treatment based off of the behavioural assessments mentioned above—resulting in misdiagnosis rates for UWS (VS) that are consistently estimated at about 40% (Andrews et al., 1996; Childs et al., 1993; Schnakers et al., 2009a,b).

In one assessment, cognitive health assessment reports generated by the analyses produced by the systems and procedures confirm if a concussion or ABI is present, the severity of the injury, specific domains of functional (e.g. neurocognitive) deficit incurred by the injury, which aid in determining areas of focus for rehabilitation.

This allows certainty in results for clinicians to provide targeted and timely methods for rehabilitation. By reducing the need for multiple tests to confirm or disprove a concussion or ABI, patients can get the help they need when they need it—as early into their recovery path as possible. The certainty additionally allows clinicians and patients to avoid trial and error in rehabilitation methods, instead focusing solely on the areas of cognitive rehabilitation the patient needs for their unique injury by following the functions identified as below the healthy norm in their cognitive health assessment report.

Applicants have developed the technology which originated from adapting these methods to assist the analysis of both coma and unresponsive wakefulness syndrome (vegetative state) patients. The system's ability to measure brain function with non-participatory requirements on the patient's behalf, has supported to confirm if brain function was present, which facilitated the patient getting into rehabilitation plans that have improved their conditions. Without this ability to identify brain function in patients who are unable to outwardly communicate, a clinic would not have been able to identify if these patients were capable of rehabilitation and eligible for it.

For coma patients specifically, cognitive health assessment according to some embodiments described herein have also been leveraged to confirm when a coma patient does in fact not have any measurable brain function, providing certainty to both the patient's clinicians and family that they are able to let go of their loved one without fear of missing a chance for rehabilitation to improve their condition.

Aside from coma, unresponsive wakefulness syndrome (vegetative state) and concussion, the technology has also been used to assess disorders of consciousness (DOC) and pediatric communication impairments (PCI).

FIG. 1A is an example system 100A for conducting cognitive health assessment that compares ERP/EEG data to methods of assessment (behavioural (always), neuro-imaging (when available)) to verify or dispute the finding and how they are relevant to the patient's functional consequences as a result of a concussion or acquired brain injury.

In FIG. 1A, a Stimulation Computer is shown as an example interface device, whereby the Stimulation Computer may be configured to present stimuli to the patient by way of headphones, display controllers, etc. The Stimulation Computer may include input receiving devices, such as microphones and a video capturing device, such as a webcam. These input receiving devices may be configured to capture responses, voluntary or involuntary, of the patient during the course of the testing. In some embodiments, involuntarily responses may be captured during the course of rest periods between stimuli, among others.

The patient is coupled with one or more electrodes (e.g., coupled to the patient's head) to capture brain function data, including event related potentials (ERPs). The electrodes may be connected to the patient in the form of a cap or other headgear, or individually.

During a test session, the computing system facilitates a series of the adapted neuropsychological tests for computer presentation, whereby a stimulus presentation program is used to take the patient through a series of steps.

The Stimulation Computer runs a presentation process to generate programmed stimuli (auditory or visual), the patient hears or sees stimulus as their EEG is recorded by the electrodes (e.g., in a cap), the electrode data are amplified using the EEG equipment and saved by the Data Visualization Computer, overlaid with stimulus markers (transferred to the Data Visualization Computer directly by the Stimulation Computer).

These stimulus tests are programmable by the user or an administrator, and the ERP tests/paradigms are programmed to record the ERP responses and correlating behavioural responses (where the patient may be required to click or press a button) at the same time to avoid needing to time-match the two after the fact.

Figure 1B:
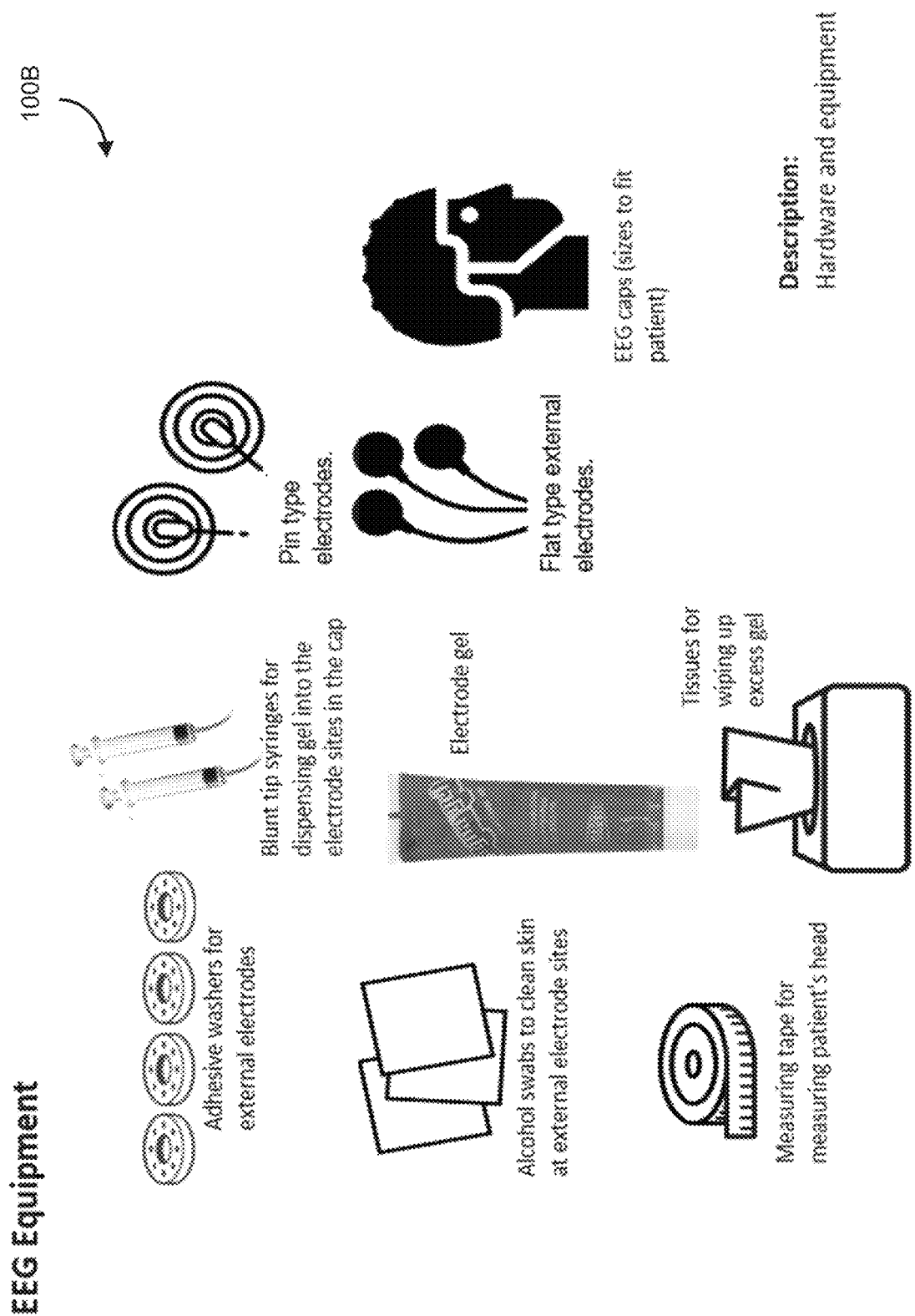
FIG. 1B is a schematic diagram depicting EEG equipment utilized in the system, according to some embodiments.

FIG. 1B illustrates example hardware 100B that can be utilized to capture the brain excitation data, including different types of electrodes, etc. The hardware may need to be adapted based on the size and profile of the individual's head. Example EEG hardware may include Biosemi™ system, a BrainProducts™ system or Compumedics Neuroscan™ system, among others.

Paradigm stimulation are delivered through the Stimulation Computer and headphones to the patient to stimulate electrical brain activity responsive to the paradigm stimulus. The electrodes capture data values, which are amplified, and provided to an acquisition mechanism and transferred to a Data Visualization Computer.

A Stimulation Computer is configured to provide stimulus markers, and in some embodiments, receive inputs through a mouse or control pad. The stored data is processed to correlate the data collected by the Data Visualization Computer in concert with the data collected with the Stimulation Computer such that brain potentials (responses) may be tracked and processed in time-coordination with the presentation of the stimuli.

The tests/paradigms have been designed with the abilities of the patient in mind (embodiments can include: auditory and vibro-tactile for coma; auditory, vibro-tactile and visual for unresponsive wakefulness syndrome (vegetative state); auditory, visual and vibro-tactile for concussion). Once set up and turned on, the tests are automated. The settings and script have been developed by the Applicants for the ease of analysis by statistical analysts, and the output from a statistical analysis software (e.g., R Studio) is designed for ease of reading by a report generator software.

Figure 2:
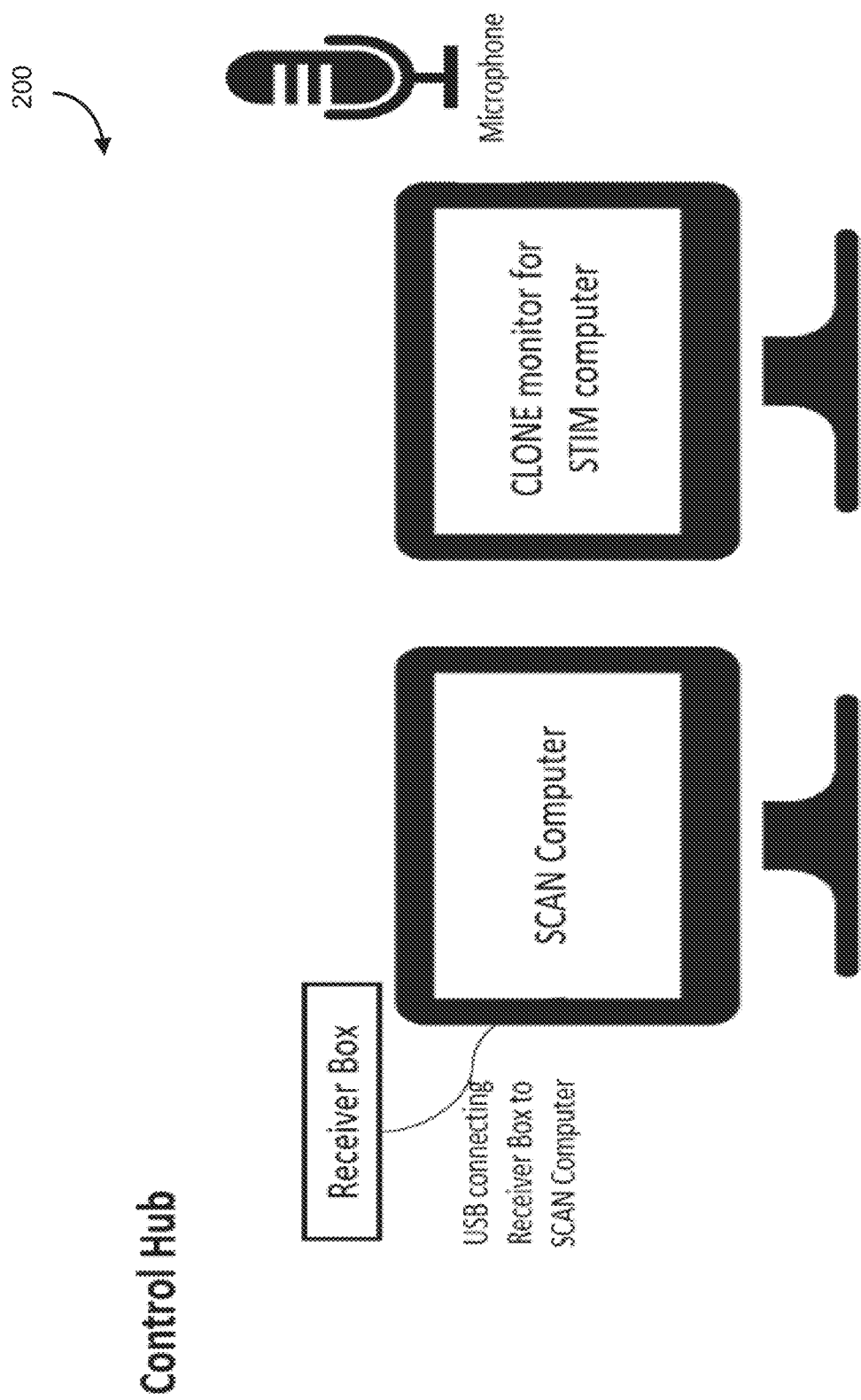
FIG. 2 is a block schematic diagram depicting example components of a system configured for cognitive health assessment, according to some embodiments.

FIG. 2 illustrates a separated Stimulation Computer and Data Visualization Computer mechanism 200, according to some embodiments. Note, however, that the Stimulation Computer and the Data Visualization Computer may be the same computer or different computers, in alternate embodiments.

In some embodiments, the Data Visualization Computer and the Stimulation Computer, can be transported such that the system can offer remote testing (on location), requiring a quiet room for patient, and space for a tester to monitor. If only 1 room is available, a patient can, for example, face a wall to minimize distractions and tester sits behind a monitor.

Figure 3A:
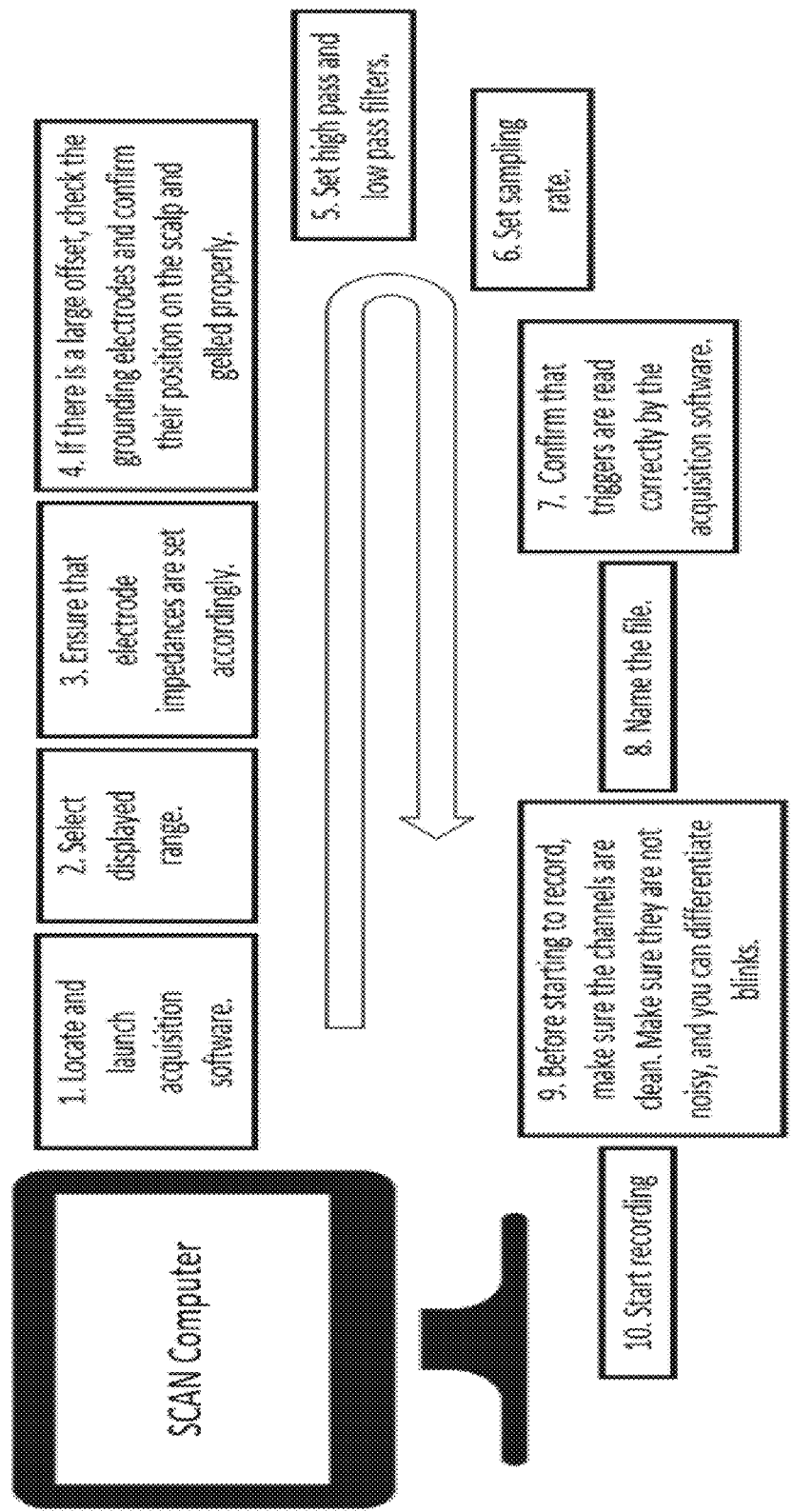
FIG. 3A is a flow diagram depicting an example method for preparing for a cognitive health assessment, according to some embodiments.

FIG. 3A is an example process diagram illustrating an initialization method 300A, according to some embodiments. A tester opens acquisition software on the Data Visualization Computer in a control room. The settings within the acquisition software for test measurements are set to be able to 'zoom in' on data produced by the testing paradigms set up in the presentation software (tests the patient is run through).

Figure 3B:
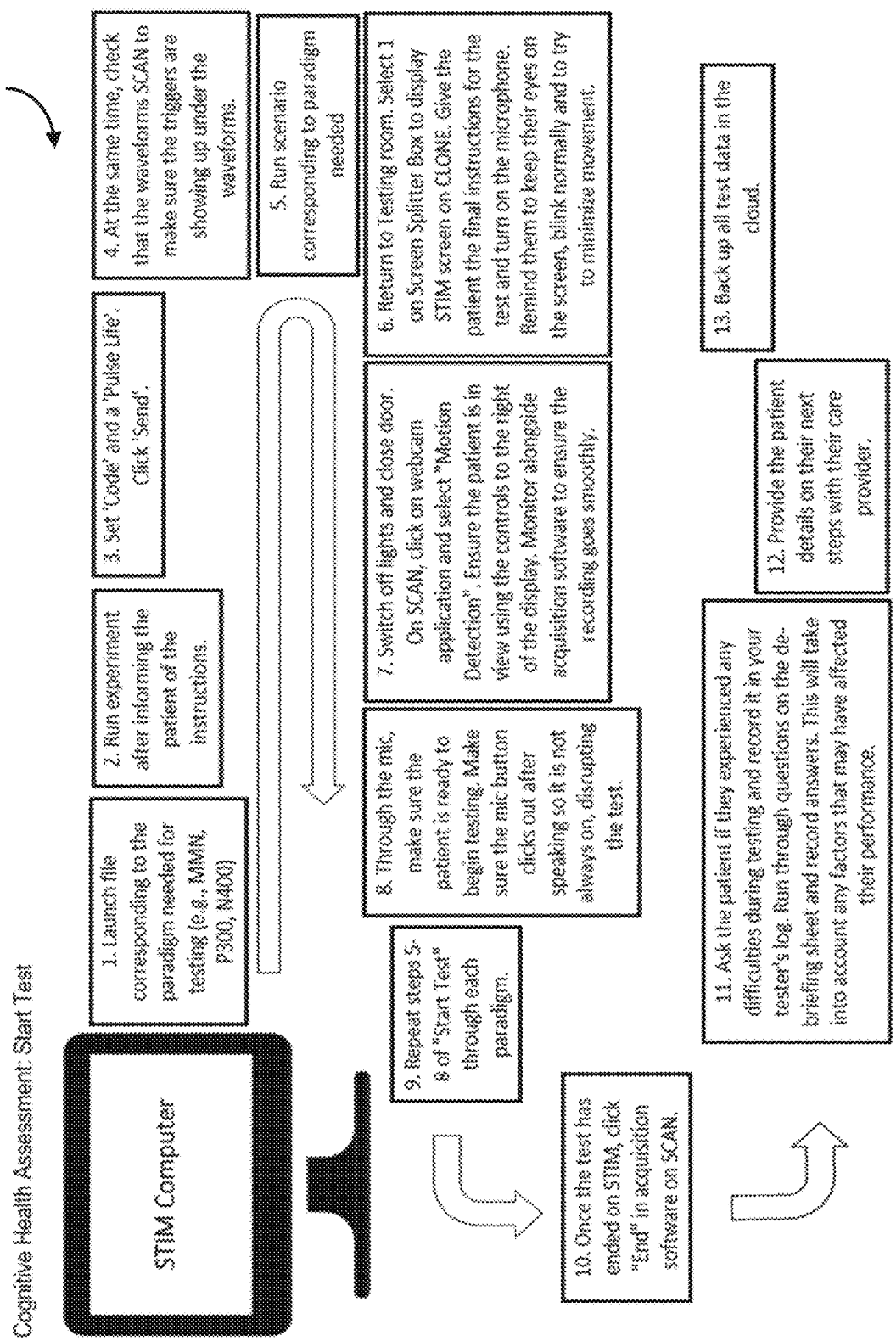
FIG. 3B is a flow diagram depicting an example method for preparing for a cognitive health assessment, according to some embodiments.

FIG. 3B is an example process 300B to start a presentation on the Stimulation Computer, and to ensure the data is being recorded and viewable on the Data Visualization Computer.

In FIG. 4, FIG. 5A, FIG. 5B, FIG. 5C, FIG. 6A, and FIG. 6B, example methods 400, 500A, 500B, 500C, and 600 are illustrated of improved cognitive health tests associated with comatose patients, unresponsive wakefulness syndrome (vegetative state) patients, concussed patients, and for general health testing.

These tests illustrate an improved, objective approach to providing assessment offerings. In additional embodiments, the tests may also be utilized for conducting mental competency assessments, elderly competency assessments, neurodevelopmental disorder competency assessments, measuring drug effects on brain function, and general brain health tracking.

The cognitive health assessment is adapted to test for:
the severity of the concussion or ABI;
specific domains of brain function (neurocognitive) deficit incurred by a concussion or ABI;
potential areas of focus for rehabilitation; and
tracking rehabilitation impact on brain function recovery.

In some embodiments, the statistical analysis, data collection and report generation steps in the assessment process are automated to reduce the turnaround time from testing to clinicians being able to review and diagnose the concussion or ABI and provide next steps for rehabilitation. Computer implemented embodiments are described herein that include a stimulus machine controlled to operate in concert with a brain function scanning machine to conduct a series of tests. The tests are designed to target different brain (cognitive) functions including language processing and comprehension abilities, high-level attention and vigilance skills, memory integrity, language comprehension, executive function, auditory and visual function, and functions of the somatosensory system (conscious perception of touch, pressure, movement, position, vibration, pain that development from contact (broadly defined) with receptors in the skin, muscles, tendons, joints, etc.).

An improved approach is described in various embodiments, wherein physical assessment devices, tools, methods, processes, and computer-readable media storing machine readable instructions, which when executed by one or more processors, perform steps of a method performing cognitive health assessment that include innovative approaches of concussion and ABI assessment to provide functional data that is a direct measurement of brain activity by using EEG and measuring event related potentials (ERPs).

The approach for performing cognitive health assessments compares ERP/EEG data to other assessments (behavioural (always), neuro-imaging (when available)) to verify or dispute the finding and how they are relevant to the patient's functional consequences as a result of an acquired brain injury.

Each battery of tests by the testing machine has a cognitive function test, according to some embodiments. An objective, sensory-based assessment tool is described herein, automatically controlling stimulus presentation and tracking. A potential benefit for patients in a clinical setting is that the objective, sensory-based assessment tool does not suffer from the "noise" caused by a patient's emotions and feelings (e.g., fears of a clinical environment and paranoia can, for other tests, lead to a false positive reading, for example, due to White Coat Syndrome). Other "noise" that may be present in subjective tests in relation to jaw clenching, and blinking, may also be accounted for.

ERP measurements that progress in complexity allow a holistic overview of the brains overall function, not just one specific indicator, as performed by alternate EEG based assessments that rely on, for example, the P300 alone.

Through this method, the assessment is able to indicate the severity of the functional consequences of injury as well as identify functional regions of the brain that are affected.

In ERP waveforms, the system assesses, among others:

Response distribution: what areas of the brain activate or "light up" when the stimuli are presented Response amplitude: strength and direction of response (positive or negative)—This is clinically relevant to identify what regions of the brain have had a functional impact due to the injury (as compared to either baselines or age/sex matched controls).

Response latency: length of delay when a stimulus is presented to when the brain responds. Similar to the amplitude, with high amplitudes being healthier and low being unhealthy, responses to tests should occur at (for example) 100, 200, 300 or 400 milliseconds dependent on what the stimulus is testing. If a latency is shown (delay in response) it is indicative of damage. The longer the delay, the more severe the damage.

Sensory Measurements: Physical Parameters

Mapping rest periods while the brain is not receiving any test stimuli. (Coma and unresponsive wakefulness syndrome (vegetative state)).

Mapping rest periods while the brain is not receiving any test stimuli. (Coma and unresponsive wakefulness syndrome (vegetative state) specifically). Useful to compare brain activity at rest to active testing, specifically for Coma and UWS patients as their level of ERP responses could be much lower than that of a concussion patient. This helps to show any minute indication of response to the testing as it will differ from what is recorded at this resting state.

N1+P2: base mental function responses to a repeated tone presentation (termed N100/P200 complex) indicative of auditory and visual processing capabilities. Both responses are generated bilaterally in the auditory cortices indicating the ability to respond to auditory stimuli and confirming ability to engage in testing without complications of core sensory issues.

N1+P2s are the earliest ERP responses measured. Viewable in any paradigm. N1s occur when a patient receives a stimulus; the N1 should always be closely followed by a P2.

Response amplitudes and latencies are unique to each patient. The size of the amplitude and latency is also dependent on the type of stimulus presented, e.g., A loud versus a soft tone. The amplitude will be higher, and latency will be earlier with louder versus soft tones.

MMN:

The MMN response, indicative of a patient's Automatic Attention, measures their ability to respond to environmental changes that are not actively attended.

MMN (negative):

Amplitude varies dependent on the stimuli presented and varies across age spans. Best compared to age/sex matched controls for 'normal' level. Closer to zero is irregular.

Should occur around 200 milliseconds, shortly before the P300. If before or after, irregular.

Cognitive Measurements: Information Processing

P300: A complex response that indicates multiple cognitive functions depending on the paradigm.

P3a: Indicative of Reactive Attention—the brain's ability to respond to stimulus deviance. The P3a is associated with brain activity related to the engagement of attention (especially orienting and involuntary shifts to changes in the environment) and the processing of novelty. For example, in a series of auditory tones, if the sound of a louder tone is inserted into a series of less-loud auditory tones, the neural response to that louder tone would contain a P3a. Accordingly, this assessment utilizes the P3a to measure "reactive" attention.

P3b: Indicative of Concentration—the mental effort of focusing one's attention on a task. The P3b response is affected by an individual's ability to distinguish rarely-occurring stimuli (called "deviants") from frequently-occurring stimuli (called "standards") in a stimulus sequence. The stimuli must be related to the task in some way. For example, in a series of tones where there are different infrequent "deviant" tones, a P3b will be elicited to the infrequent stimuli when the patient is asked to attend to and differentially respond (i.e., mouse click) to the "standard" and "deviant" tones.

P3b: Indicative of Working Memory—a cognitive system responsible for temporarily holding information available for processing. The P3b measures working memory presence and efficiency. The response is obtained in response to complex visual pattern stimuli, some of which are repeated throughout the sequence. The client's task requires maintaining working memory templates of what stimuli are and are not repeated and responding (mouse click) accordingly. The P3b reflecting working memory differs from other P3b responses because it occurs at a later latency and has a different voltage distribution across the scalp, indicating a different group of neural generators producing the response.

P300 (positive): Amplitude varies dependent on the stimuli presented and varies across age spans. Best compared to age/sex matched controls for 'normal' level. Closer to zero is irregular.

Should occur at 300 milliseconds. If before or after, irregular.

N400: Complex Language Comprehension response that reflects language comprehension integrity—indicative of a patient's ability to process word and phrase meanings, sentence grammar, and discourse.

N400 (negative): Amplitude varies dependent on the stimuli presented and varies across age spans. Best compared to age/sex matched controls for 'normal' level. Closer to zero is irregular.

Should occur at 400 milliseconds. If before or after, irregular.

N2b: Indicative of Executive Functions—a collection of interacting processes that represent a set of skills that all work to make it possible for an individual to make plans, anticipate consequences of behaviour, organize schedules and generally function competently in life and society. The complexity of executive functions means that the skill sets involved are often represented by a range of ERP components with the most notable being the N2b. The N2b reflects focused attention and concentration that enables monitoring of one's own behaviour in order to inhibit a response to one type of stimulus while continuing to respond to another type of stimulus.

N2b reflects an indicator of the cognitive network comprised of multiple processes that together enable complex behavior.

N2b (negative): Amplitude varies dependent on the stimuli presented and varies across age spans. Best compared to age/sex matched controls for 'normal' level. Closer to zero is irregular.

Should occur at 200 milliseconds.

A complex cognitive function test such as testing Language Comprehension requires a patient's active attention as it is a conscious choice to listen to what a person is communicating, and memory to 1) retain what was said to be able to respond, and 2) pull from memory to identify language and understand its meaning.

The definitions and the outcomes of each ERP responses (generated in the Cognitive Function Tests) are most easily clinically relatable to neuropsychologists as the data matches testing that they would otherwise complete offline with manual measurements, which are inherently subjective. The testing validates the outcomes of these tests and captures the responses as purely objective data, extracting any potential for interpretation.

Although the specific ERP responses are outside the existing measures occupational therapists (OTs), physical therapists (PTs) and speech language pathologists (SLPs) utilize (today), reports generated by the system described herein are also extremely clinically valuable to these types of therapeutic interventions in addition to neuropsychology as they: track progress, and with repeated assessments throughout rehabilitation, the reports provide a tool for tracking a patient's progress, and aids in confirming effective methods of treatment for the injury and for the patient.

Functional improvements are measurable approximately 30 days before those improvements translate to behaviour, which provides early encouragement and verification that the chosen methods of rehabilitation are working.

The reports also help set recovery expectations, whereby the reports help the clinician, patient and family understand the length of time, and level of involvement required in a rehabilitation plan. The reports also provide benchmarks of the patient's 'norm' against age/sex matched controls and their personal benchmarks (when available) to confirm if the patient is ready to return to activities or return to regular activity or play without any uncertainty, for concussed patients specifically.

The reports, for example, help a clinician indicate if the patient has a concussion or ABI, and what type it is (e.g., differentiating between coma and/or unresponsive wakefulness syndrome (vegetative state), and if a concussion is present), the severity of that concussion or ABI, the areas of function that are impacted.

Reports generated may include, for example:

Patient reports for specific conscious state: 1) coma, 2) unresponsive wakefulness syndrome (vegetative state), and 3) concussion.

Reports formatted specifically for clinical rehabilitation and personal injury law firms, among others.

In some embodiments, the reports, in data structure formats, are adapted for conducting downstream machine learning (e.g., supervised learning) based on training, validation, and test pairs of data features and outcomes. Accordingly, over time, the weights may be modified to overall track towards an improved accuracy (e.g., sensitivity and/or specificity).

FIGS. 4, 5A and 5B, and 5C are directed to patients who are comatose or experiencing unresponsive wakefulness syndrome (vegetative state). Example cognitive function tests include;

1. MMN
2. P300
3. N400+PMN
4. Resting State

FIG. 6 is directed to patients who are suspected of having concussions. Example cognitive function tests include;

1. P300
2. N400
3. MMN
4. N2b/P3b

N1+P2s are measured within each paradigm

Referring back to FIG. 4, FIG. 4 is a flow diagram depicting an example method for a cognitive health assessment tailored for patients who are comatose, according to some embodiments.

A baseline set of behavioural tests are conducted to compare results to the EEG/ERP cognitive function test outcomes illustrative of the improved approaches described in some embodiments.

An example of behavioural tests used is the Glasgow Coma Scale (GCS). The Glasgow Coma Scale (GCS) can be utilized as it is one of the most commonly practiced Coma Scales. The Coma Scale measures basic observable behavioural biological function (eye, verbal, motor responses) in a patient. The GCS measures different levels of function such as eye opening, verbal response and motor response. Generally, the scoring from low to high reflects poor to good current state, which in turn reflects poor to good prognostics (outcome).

Cognitive function tests are then conducted using EEG, having the following approaches, according to some embodiments:

Sequence 1: Automatic Attention (Measure Mismatch Negativity (MMN))

The system begins playing consistent auditory stimuli to the patient with occasional outlier tones without any instruction to listen for specific tones or changes.

Sequence 2: Reactive Attention, Concentration, Working Memory (P300s+N2b)

Progressing from MMN, the system presents a screen to the patient (or generates audible instructions), "You are going to hear this tone again, count its occurrences if you can. You are also going to hear a new tone (deviant) that is different than this tone you've heard. Pay attention to this." The patient now has the instruction to identify the differences between tones. The purpose of the test is to look for a more complex response.

While playing the standard tone intermixed with the periodic deviant, the system will monitor for an N2b, which has similar timing to the MMN but occurs when a patient is paying attention. The N2b occurs at the same time as an MMN, and usually has a larger amplitude. This will be assessed in comparison to the P300.

Deviant examples are: an alternate tone, stating the patient's name, stating a random word e.g., "Tree", a recognizable sound such as a dog bark/phone ringing.

Each deviant stimulus (e.g., tone, name, random words, random noises) should garner a slightly different, uniquely measurable P300 response. For example, a patient's P300 response should be slightly different than their response to any other deviant sound, as showing recognition of the patients' name can provide a strong indication of consciousness.

Sequence 3: Language Comprehension (N400s) and Phonological Mapping Negativity (PMN)

Basic (nonsensical sentences): Tests language processing+vocabulary knowledge

The system will output a series of sentences to the patient such as, "The pizza was too hot to eat", "The pizza was too hot to sing".

The patient will show an N400, if they are in a conscious state, to the word "sing" in the example sentences because it is not a verb that makes sense within this sentence.

Complex (cloze sentences): Tests semantic prediction

The system is controlled to output sentences with subtle inaccuracies such as, "The pigs wallowed in the pen" vs "The pigs wallowed in the mud". If a patient is showing N400 responses, and complex sentences are recognized, it shows the level of intact language receptive abilities a patient is displaying, for example, high level of language function.

Phonological Mapping Negativity (PMN)

The PMN is a language related ERP component that occurs in response to phonological processing of speech. While it is independent of the semantically related N400, it often occurs with it during tests that manipulate how unexpected a word is within speech. That is, it responds to violations of expectations so that it will occur if a patient expects a specific word, but an alternate is in its place. E.g., The patient may expect to hear the word "mouse" in the sentence "she chased the mouse with a broom", but instead heard "lampshade".

Sequence 4: Resting State

Brain activity is mapped when no stimuli are present with the intent of measuring frequency and power characteristics of the patient's EEG.

WITHIN SEQUENCES: Measure N1+P2s

N1+P2s are measured within each paradigm. Responses prior to MMN, P300, N400 or PMN. The responses are indicative of auditory function. If N1 and P2s are not detected, auditory brain stem responses and middle latency responses are further examined to check the integrity of the auditory pathway systems.

Figure 5A:
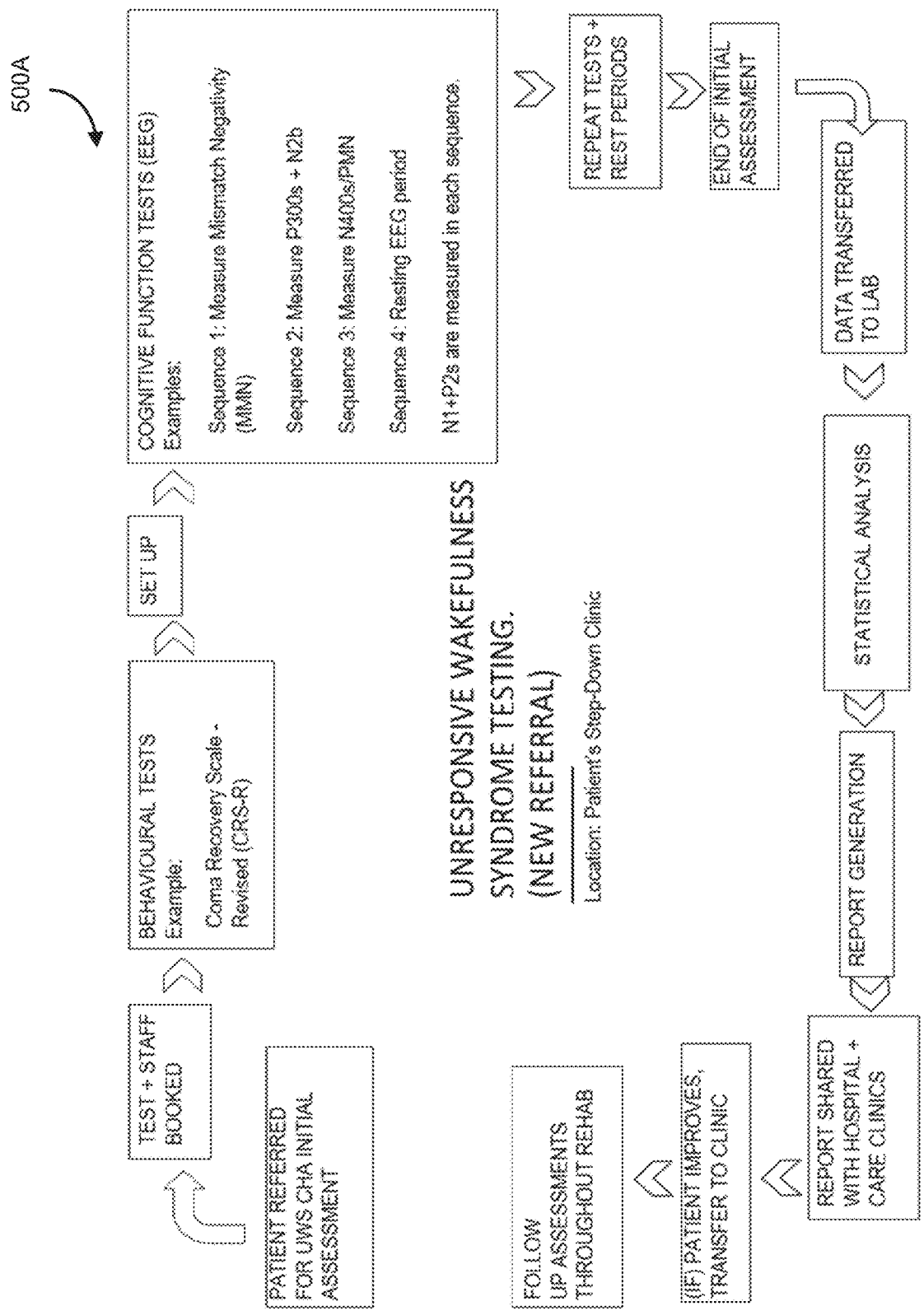
FIG. 5A is a flow diagram depicting an example method for a cognitive health assessment tailored for unresponsive wakefulness syndrome (UWS) (vegetative state) patients (new patients), according to some embodiments.
Figure 5B:
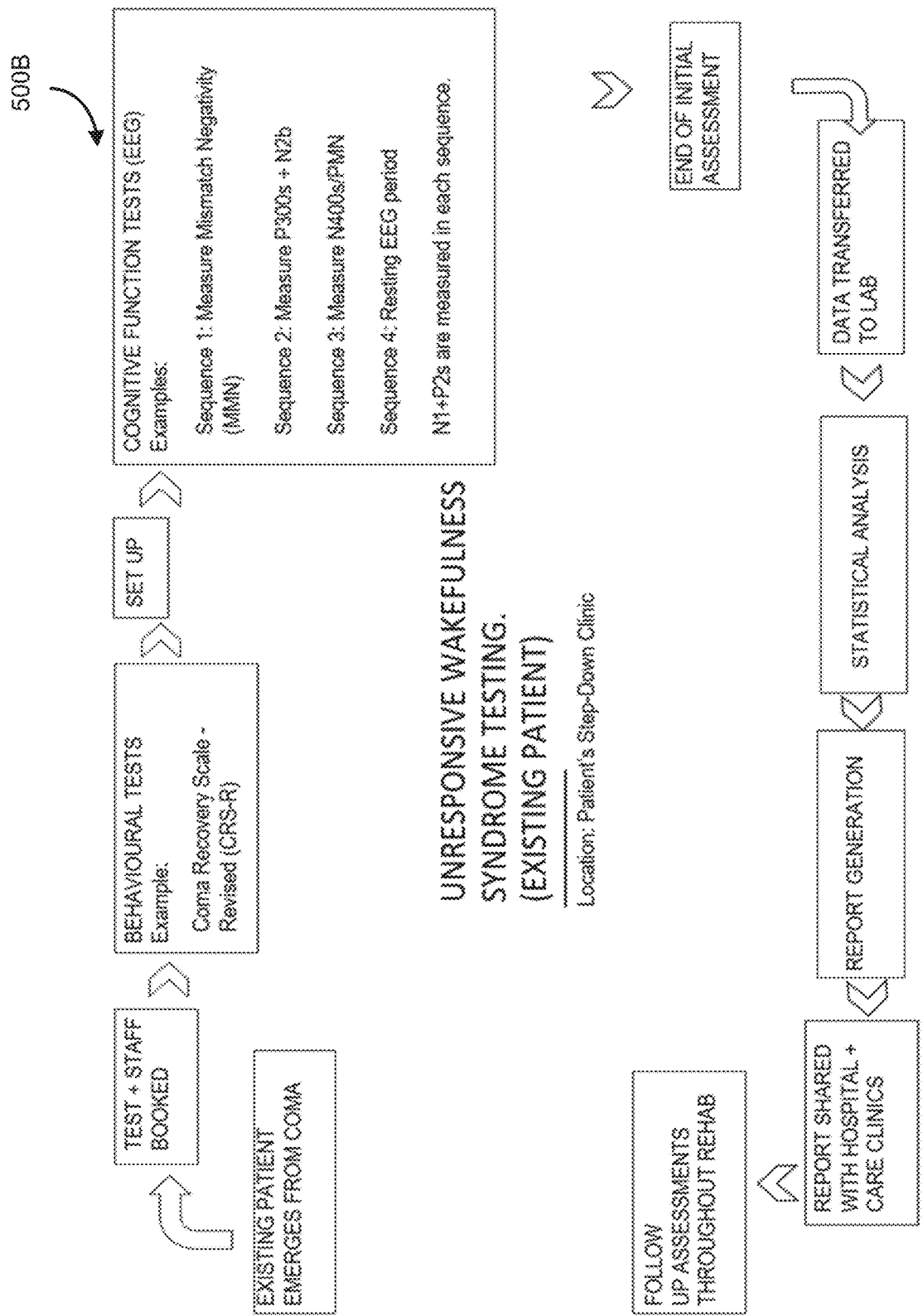
FIG. 5B is a flow diagram depicting an example method for a cognitive health assessment tailored for unresponsive wakefulness syndrome (vegetative state) patients (follow up assessment for patients who have emerged from coma), according to some embodiments.
Figure 5C:
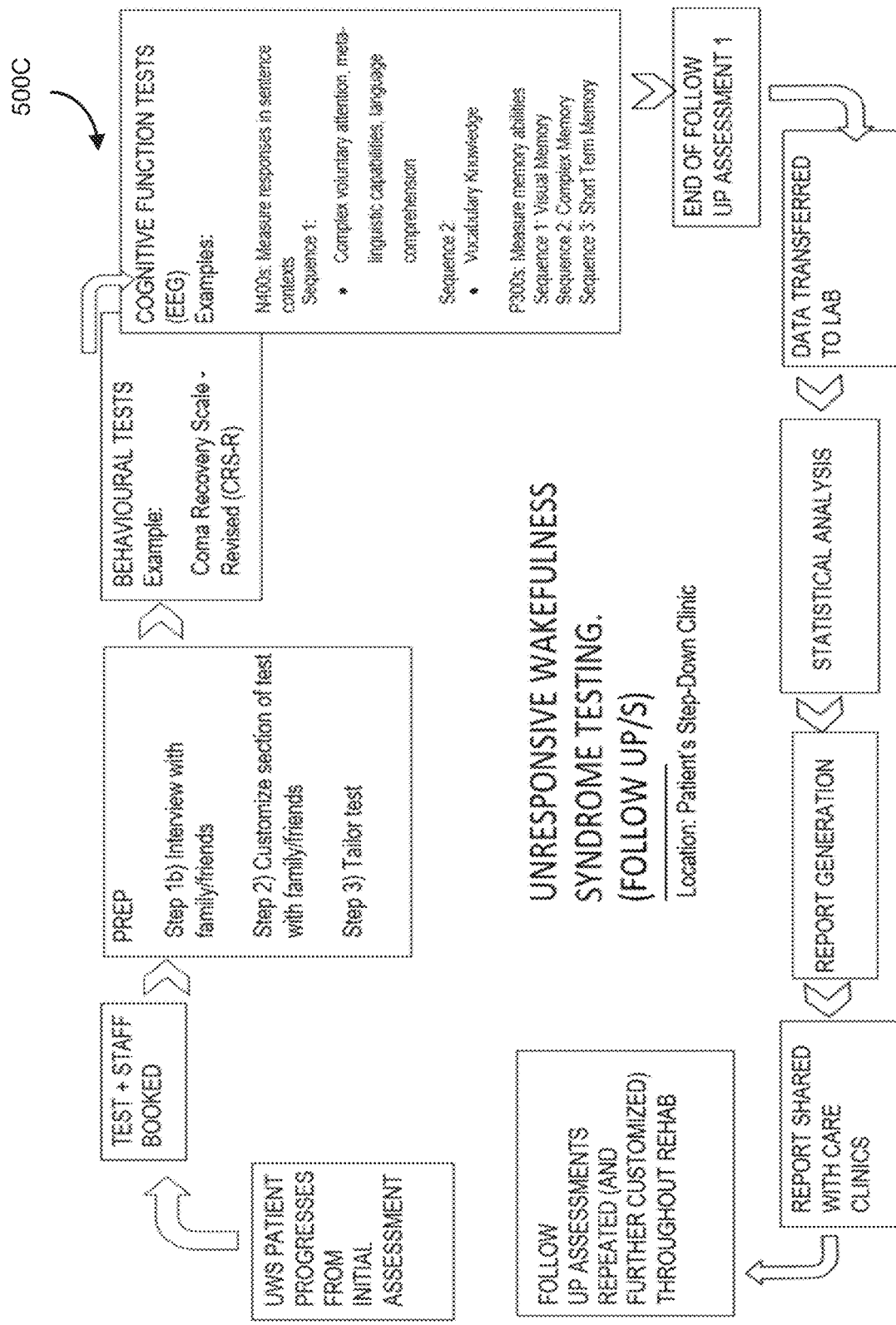
FIG. 5C is a flow diagram depicting an example method for a cognitive health assessment tailored for unresponsive wakefulness syndrome (vegetative state) patients (existing patient follow-ups), according to some embodiments.

FIG. 5A, FIG. 5B and FIG. 5C are flow diagrams depicting an example method for a cognitive health assessment tailored for unresponsive wakefulness syndrome (UWS) (vegetative state) patients (new patients/existing patients), according to some embodiments.

Due to the complexity of unresponsive wakefulness syndrome (vegetative state), follow up assessments have been outlined in addition to the initial assessment to summarize how testing can be customized to pinpoint functional abilities in a patient who is not able to communicate with other methods (speech, writing, signing) other than through the brain measures/ERPs the system records.

Figure 4:
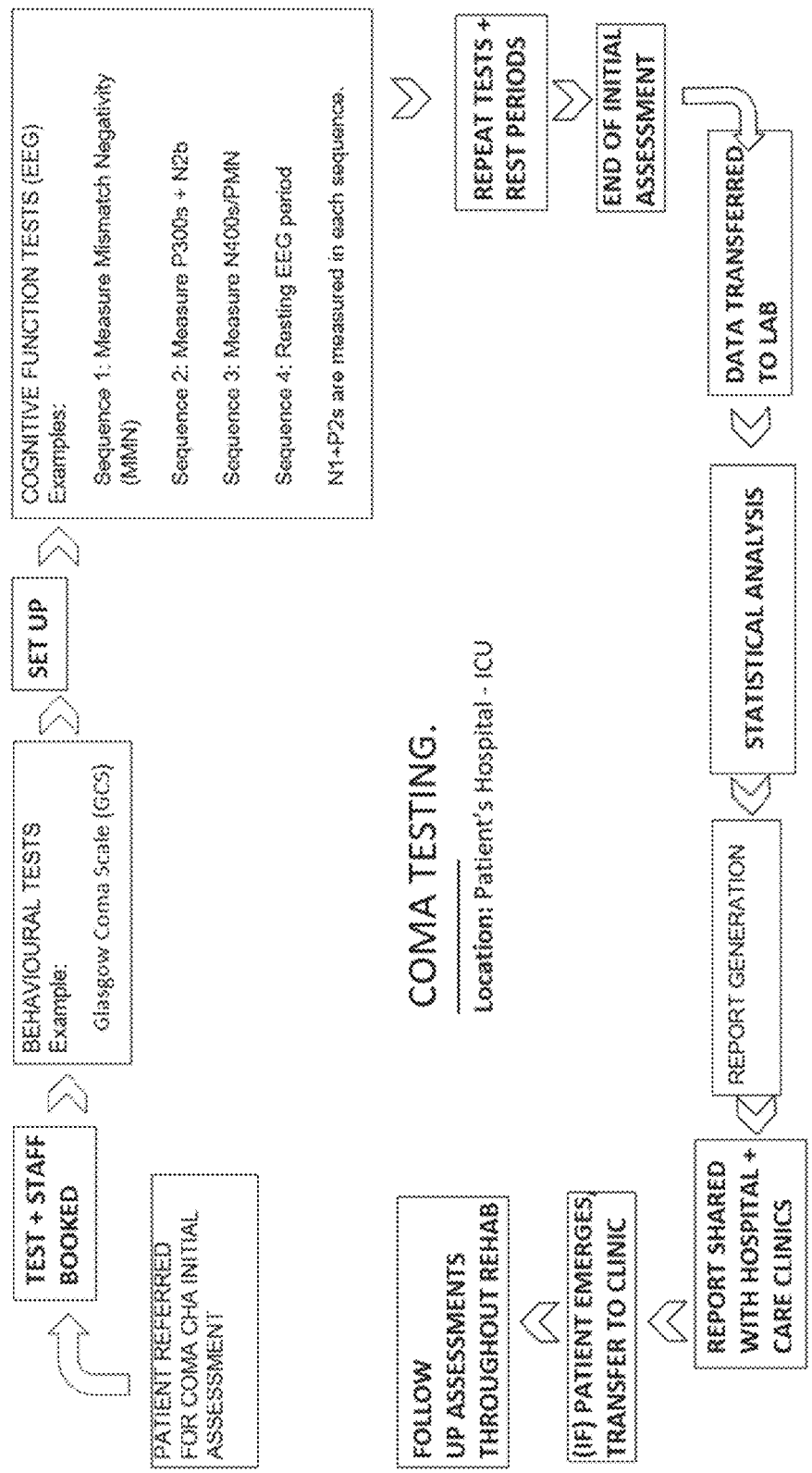
FIG. 4 is a flow diagram depicting an example method for a cognitive health assessment tailored for patients in comas, according to some embodiments.

Similar to FIG. 4, behavioural tests are conducted (e.g., Coma Recovery Scale—Revised analysis to track patients who have emerged from comas).

For unresponsive wakefulness syndrome (vegetative state) patients, cognitive function tests are conducted using EEG, having the following approaches, according to some embodiments:

INITIAL ASSESSMENT
   Step 1: If the system tested the patient in coma, follow the same process as Coma Cognitive Health Assessment to assess changes in function. If the system did not test the patient in Coma, follow the same process as Coma Cognitive Health Assessment to create an initial report.

FOLLOW UP ASSESSMENT/S
   Step 1a: (For patients whose initial assessment occurred while diagnosed as being in an UWS state) Re-administer initial assessment to check for progress and assess if ready to proceed with additional testing.

Step 1b: (For patients whose follow up assessment after Coma emergence while in an UWS state/For UWS patients who have shown progress in follow up assessments)
   Consult with family/friends of the patient with a standardized questionnaire Questions examples include:
   Who are some of patient X's favourite celebrities? (Political figures, athletes, actors, etc.)
   What is their favourite band/musician/genre?
   What are some of their favourite topics of conversation?
   Describe their day-to-day life—locations, interactions with people, commute routes etc.
   Step 2: Customize section of assessment with family/friends involvement to test for voice recognition. E.g., Have family/friends record a sequence of names that includes the patient's.
   Step 3: Tailor assessment to create stimuli that will work for the patient's age, musical preferences, famous faces, familiarities of environment as indicated from the interview in Step 1b.
   Behavioural tests are conducted (e.g., Coma Recovery Scale—Revised analysis).

FOLLOW UP ASSESSMENT CONTINUED
   N400 sequences: Complex Language Comprehension with patient customized tests. Measuring N400s—Negative response at 400 milliseconds in a healthy person.
   Sequence 1: Complex voluntary attention, meta-linguistic capabilities, language comprehension (recognizing abnormalities in sentences)
   This sequence is used to identify if a patient can recognize if the semantics of a sentence do not make sense, as well as their knowledge of how things function in the real world. If a patient can identify that "socks do not go with coffee" (for example), the system scales the subtlety of the sentences from less subtle to more subtle to assess what the extent of the patient's comprehension abilities. For example, for more subtlety, the system will add sentences that are not semantically incongruous, but instead have subtle irregularities.
   Basic (nonsensical sentences): Tests language processing+vocabulary knowledge to ensure patient stability from initial UWS assessment.
      The system will output a series of sentences to the patient such as, "The pizza was too hot to eat", "The pizza was too hot to sing".
   The patient will show an N400, if they are in a conscious state, to the word "sing" in the example sentences because it is not a verb that makes sense within this sentence.
   Complex (cloze sentences): Tests semantic prediction
      The system is controlled to output sentences with subtle inaccuracies such as, "The pigs wallowed in the pen" vs "The pigs wallowed in the mud". If a patient is showing N400 responses, and complex sentences are recognized, it shows the level of intact language receptive abilities a patient is displaying, for example, high level of language function. These tests provide additional layer of complexity from initial assessment: as baseline cloze sentences required the patient to identify when a word in the sentence isn't quite right. This added level will leave a word out of a sentence, e.g., "He stopped to talk to her about the . . . ".

The patient should show a response to the missing word due to it being unfinished. The end of the sentence is not obvious, so the N400 should be a strong response as the patient should wonder what is missing from the sentence. Nothing is 'wrong' with these unfinished sentences. They are used to measure how well a patient can predict how the sentence will end (semantic prediction).

Sequence 2: Vocabulary Knowledge (in isolation as opposed to sentences in Sequence 1 basic and advanced N400 testing)

To test to see if a patient has lost large portions of their vocabulary, for example, the Peabody Picture Vocabulary Test can be used to test patients who have their eyes open. For example, the system will show a picture of a cat and will present an accurate word match for the picture (cat) or, will present an inaccurate word match for the picture (telephone). N400s and proceeding responses are examined, responses should be large when a picture and word do not match. If a patient is not showing N400 responses for these mismatches, it explains they are not responding well to language because they have lost some elements of vocabulary knowledge. Vocabulary Knowledge tests are a pinnacle of conscious measurements because they require the complex levels of cognitive function. Vocabulary used is of varying sophistication.

P300s & related component sequences: Memory Tests utilize industry standard methods (such as "Famous Faces", "Continuous Visual Memory Test", and "Digit Span"—some examples but can be interchanged) that have also been adapted for computer presentation to record ERPs, integrating the family/friend interview responses to be most relevant to the patient and what they were familiar with prior to injury.

Sequence 1: Visual Memory (requires vision) Facial recognition leverages test called "Famous Faces". From the consultation with the family/friends, the test is geared to the patient's age group, and ensured to include faces they will recognize, and ones that they have not seen (non-famous faces). When a patient sees a face they have seen before in life, they will show a P300 brain response. If they do not show this response, the system detects the patient does not have memory for faces. In addition, the test is further customized by including images provided by the family of the patient's family members and friends.

Sequence 2: Complex Memory—Shape recognition leverages the "Continuous Visual Memory Test" (CVMT). Testing shape recognition is valuable for patients with a language barrier. It is used to determine if the cognitive barrier is due to language or memory alone. The system shows the patient geometric shapes and will periodically repeat several of them, asking the patient to mentally identify when they see one repeated. This will indicate the integrity of their non-verbal visual memory.

Sequence 3: Short Term Memory: The "Digit Span" test is used to examine short-term memory. The system will show on a screen or audibly state (depending on the patient's condition) 3 or more digits. When a digits sequence is presented followed by an identical or different ordering of the digits, if the patient recognizes an out-of-sequence digit, they will show a P300 response.

Figure 6A:
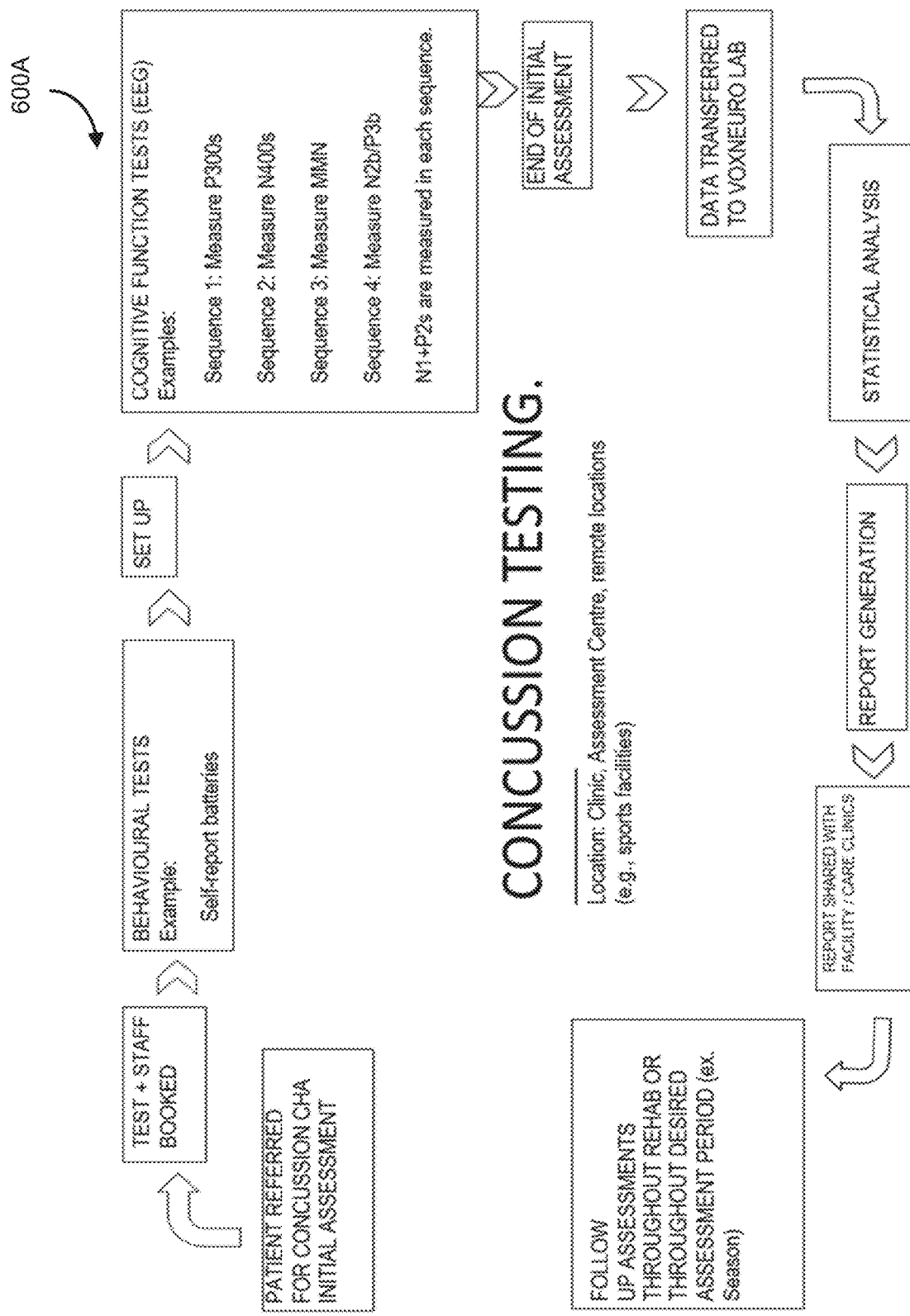
FIG. 6A is a flow diagram depicting an example method for a cognitive health assessment tailored for patients with concussions, according to some embodiments.

FIG. 6A is a flow diagram 600A depicting an example method for a cognitive health assessment tailored for patients with concussions, according to some embodiments.

Behavioural Tests: The system leverages industry standard behavioural assessments such as self-reported batteries test results, a selection are included as part of the assessment. These have been selected, as they are the most popular existing behavioural methods of assessments used by rehab clinicians.

Like behavioural tests of the Coma and UWS cognitive health assessments, these are included to bridge the gap between current gold standards of concussion and ABI assessment, by comparing their subjective results to the objective results of the EEG portion of the cognitive health assessment. This comparison confirms (or disproves) the validity of the behavioural results. This is especially important for concussion assessments as results are often purposefully inaccurately reported by the patient to speed up their return to activity/play, or conversely to be removed from work/activity or provided accommodations for an injury. These specific methods are very commonly used for athletes preseason and during season to track progress but have a huge margin for error due to them being subjective and dependent on the patient's disclosure. By comparing the claims to the EEG/ERP findings, it can confirm accuracy or identify false claims.

Self-Reported Batteries

Symptoms are self-reported by the patient, most commonly on a symptom scale and checklists (e.g., How bad are your headaches on a scale of 1-10?).

The GAD7, PHQ9, SF-36, and PCSS self-report inventories are used to evaluate the general health and well-being of the patient.
  GAD7 evaluates anxiety
  PHQ9 evaluates general health,
  SF-36 evaluates general health,
  PCSS evaluates post-concussion symptomatology.

Cognitive function tests

Sequence 1: P300s—Reactive Attention and Working Memory

PART 1: Tester instructs the patient that they will hear a series of repeated tones. Each time that standard repeated tone occurs, the patient is instructed to click left with the mouse. At any point that the patient hears a deviant tone, they are instructed to right click on the mouse. Throughout this test, the patient is hearing the tones through headphones, and looking at a white target on a black screen—this helps to have the patient keep their head steady and reduce recorded 'noise' in the EEG recordings. In some embodiments, the system generates the instructions, alongside the tones and records the measurements.

PART 2 (Counterbalance): The tester instructs the patient that they will hear a series of repeated tones. This time, each time a standard repeated tone occurs, the patient is instructed to click right with the mouse. Each time a deviant tone appears the patient is instructed to click left with the mouse. This is the opposite of the first step in this paradigm.

Sequence 2: N400—Language Comprehension: The tester instructs the patient to listen to a variety of sentences and pay attention to whether they make sense. The patient is instructed to click left to ones that make sense, and right to ones that do not. Basic (nonsensical sentences): Tests language processing+vocabulary knowledge The system will present a series of sentences to the patient such as, "The pizza was too hot to eat", "The pizza was too hot to sing".

The patient will show an N400, if they are processing language and maintaining attention throughout the sentence. The response will be to the word "sing" in the example sentences because it is not a verb that makes sense within this sentence. In the Concussion Cognitive Health Assessment, the responses are examined more specifically for their strength and latency than in the coma and UWS assessments, that are looking for presence versus absence of response.

Complex (cloze sentences): Tests semantic prediction

The system is controlled to output sentences with subtle inaccuracies such as, "The pigs wallowed in the pen" vs "The pigs wallowed in the mud". If a patient is showing N400 responses, and complex sentences are recognized, it shows the level of intact language receptive abilities a patient is displaying, for example, high level of language function.

Sequence 3: Automatic Attention (MMN)—The tester instructs the patient to watch a video without its regular audio track. They will hear beeps throughout the clip but have not been instructed to listen for them.

Sequence 4: Working Memory (P3b)

A cognitive system responsible for temporarily holding information available for processing. The P3b measures working memory presence and efficiency. The response is obtained in response to complex visual pattern stimuli, some of which are repeated throughout the sequence. The client's task requires maintaining working memory templates of what stimuli are and are not repeated and responding (mouse click) accordingly. The P3b reflecting working memory differs from other P3b responses because it occurs at a later latency and has a different voltage distribution across the scalp, indicating a different group of neural generators producing the response.

Sequence 5: Executive Function (N2b/P3b)

The Executive Function N2b and P3b responses indicate a cognitive network comprised of multiple processes that together enable complex behaviour.

N2b/P3b measures the collection of interacting processes that represent a set of skills that all work to make it possible for an individual to make plans, anticipate consequences of behaviour, organize schedules and generally function competently in life and society. The complexity of executive functions means that the skill sets involved are often represented by a range of ERP components with the most notable being the N2b. The N2b reflects focused attention and concentration that enables monitoring of one's own behaviour in order to inhibit a response to one type of stimulus while continuing to respond to another type of stimulus.

The patients will listen to or watch complex visual or auditory pattern stimuli, some of which are repeated throughout the sequence while the patient has been instructed to actively ignore specific visuals or auditory tones or patterns, and recognize or respond to alternate repeated visuals or auditory tones or patterns.

WITHIN SEQUENCES: Measure N1+P2s

N1+P2s are measured within each paradigm. Responses prior to MMN, P300, N400 or PMN. The responses are indicative of auditory function. If N1 and P2s are not detected, auditory brain stem responses and middle latency responses are further examined to check the integrity of the auditory pathway systems.

Figure 6B:
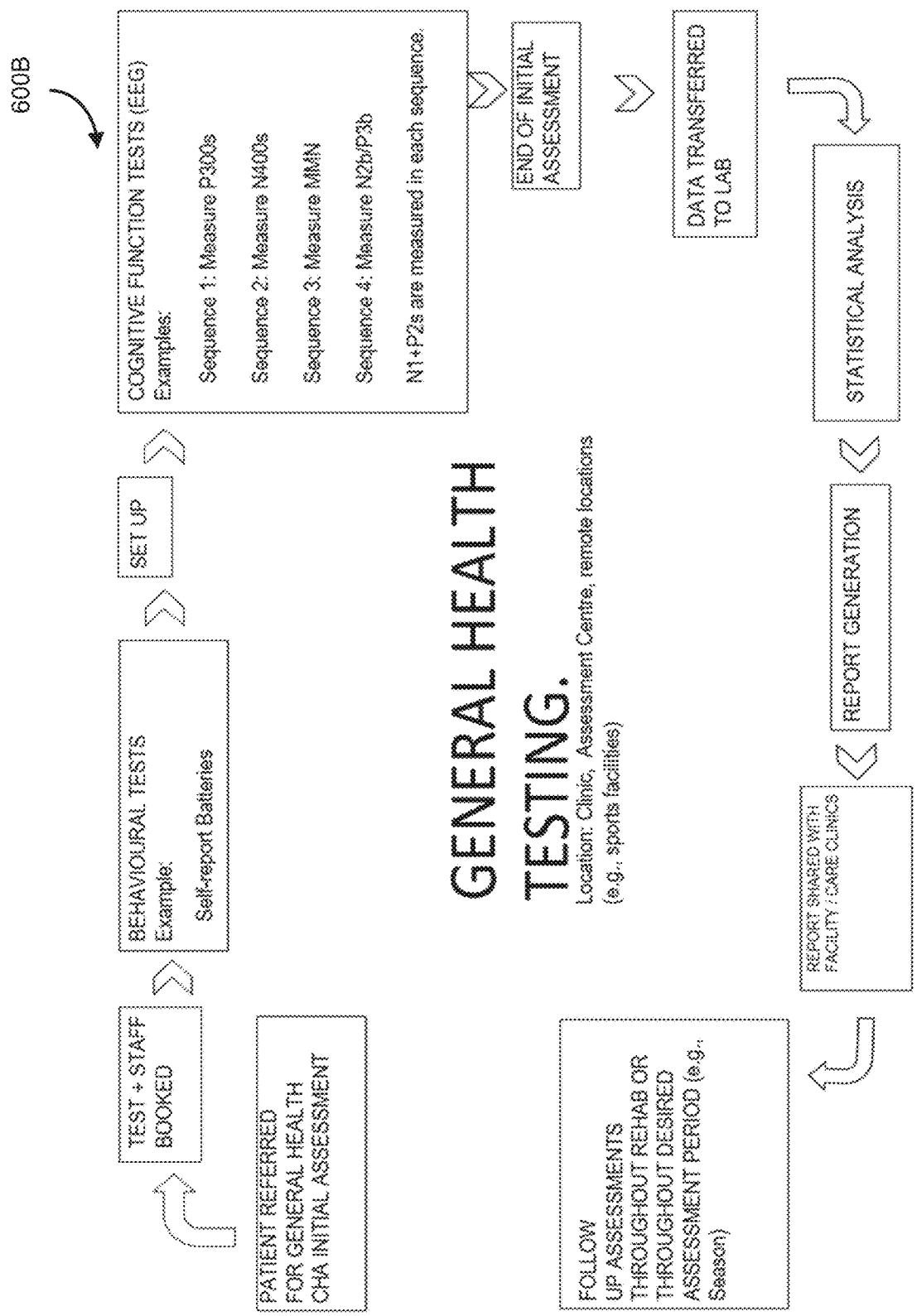
FIG. 6B is a flow diagram depicting an example method for a cognitive health assessment tailored for clients seeking a general cognitive health assessment, according to some embodiments.

FIG. 6B is a flow diagram 600B depicting an example method for a cognitive health assessment tailored for clients seeking a general cognitive health assessment, according to some embodiments.

The tests may also be utilized for conducting mental competency assessments, elderly competency assessments, neurodevelopmental disorder competency assessments, measuring drug effects on brain function, and general brain health tracking.

FIG. 7A, FIG. 7B, FIG. 7C, and FIG. 7D show example brain sensor waveform diagrams, according to some embodiments.

Figure 7A:
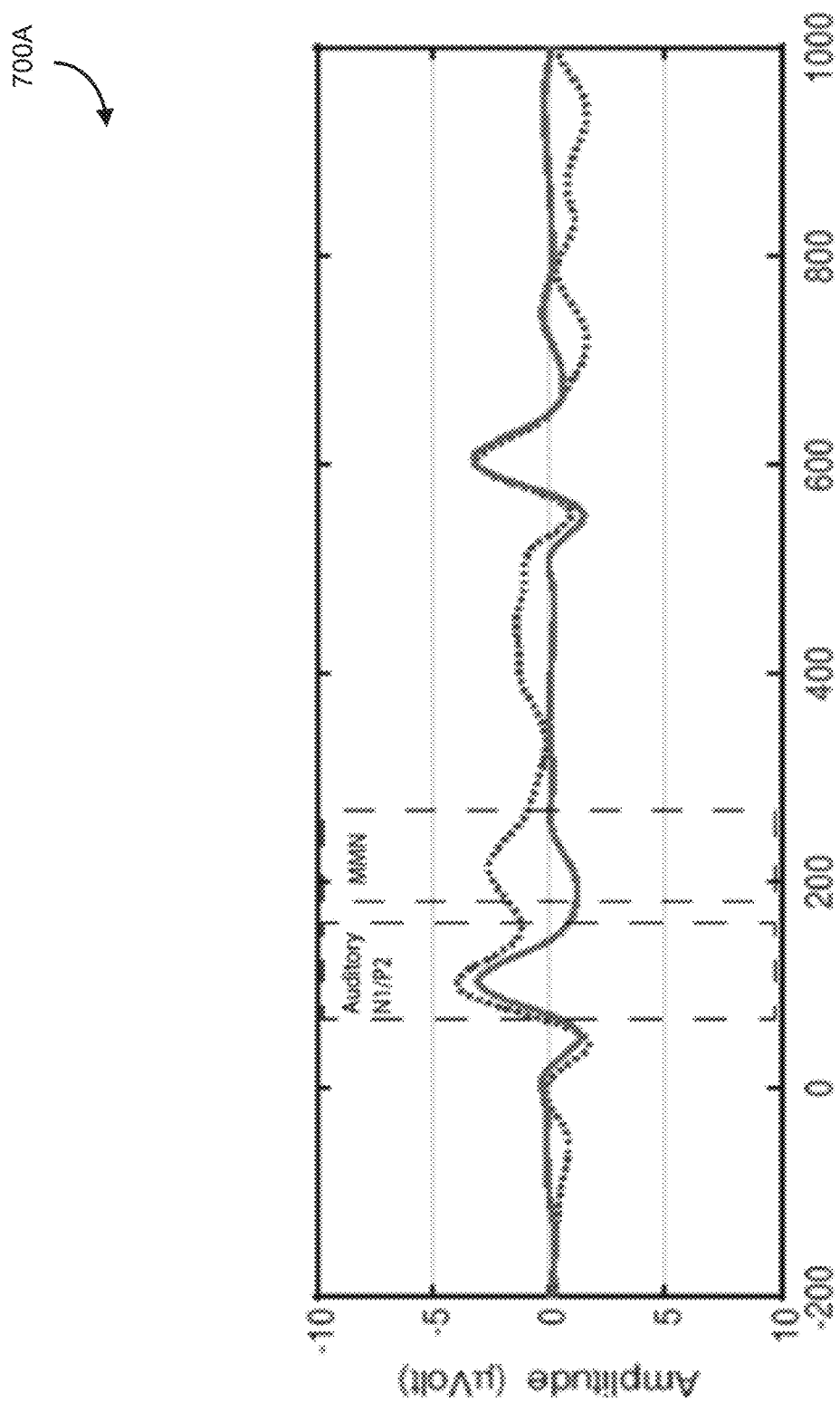
FIG. 7A, FIG. 7B, FIG. 7C, and FIG. 7D show example brain sensor waveform diagrams, according to some embodiments.

FIG. 7A includes the example graph 700A, showing example auditory N1/P2 responses as well as example MMN responses showing amplitude charted against time.

Figure 7B:
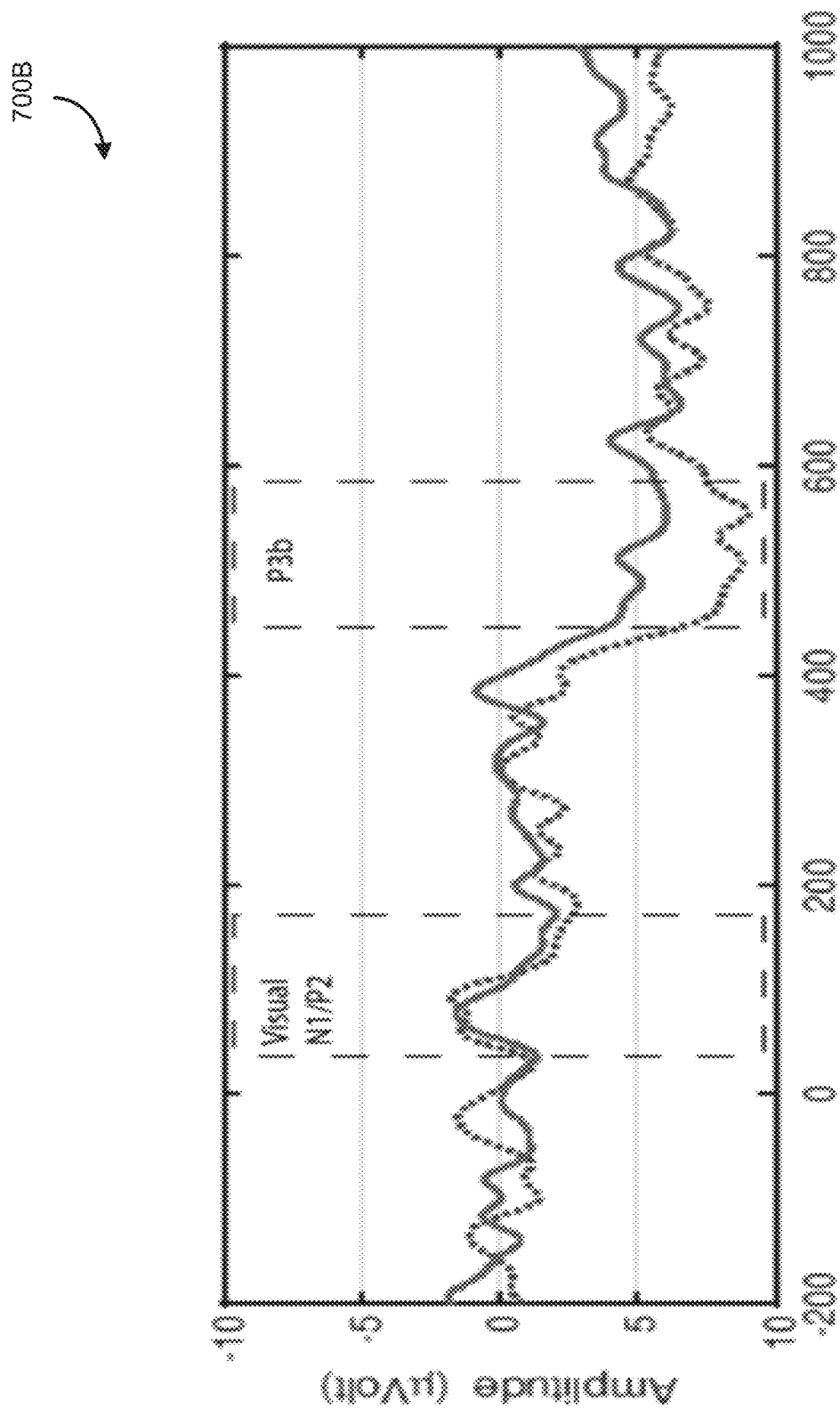

FIG. 7B includes the example graph 700B, showing example visual N1/P2 responses as well as example P3b responses showing amplitude charted against time.

Figure 7C:
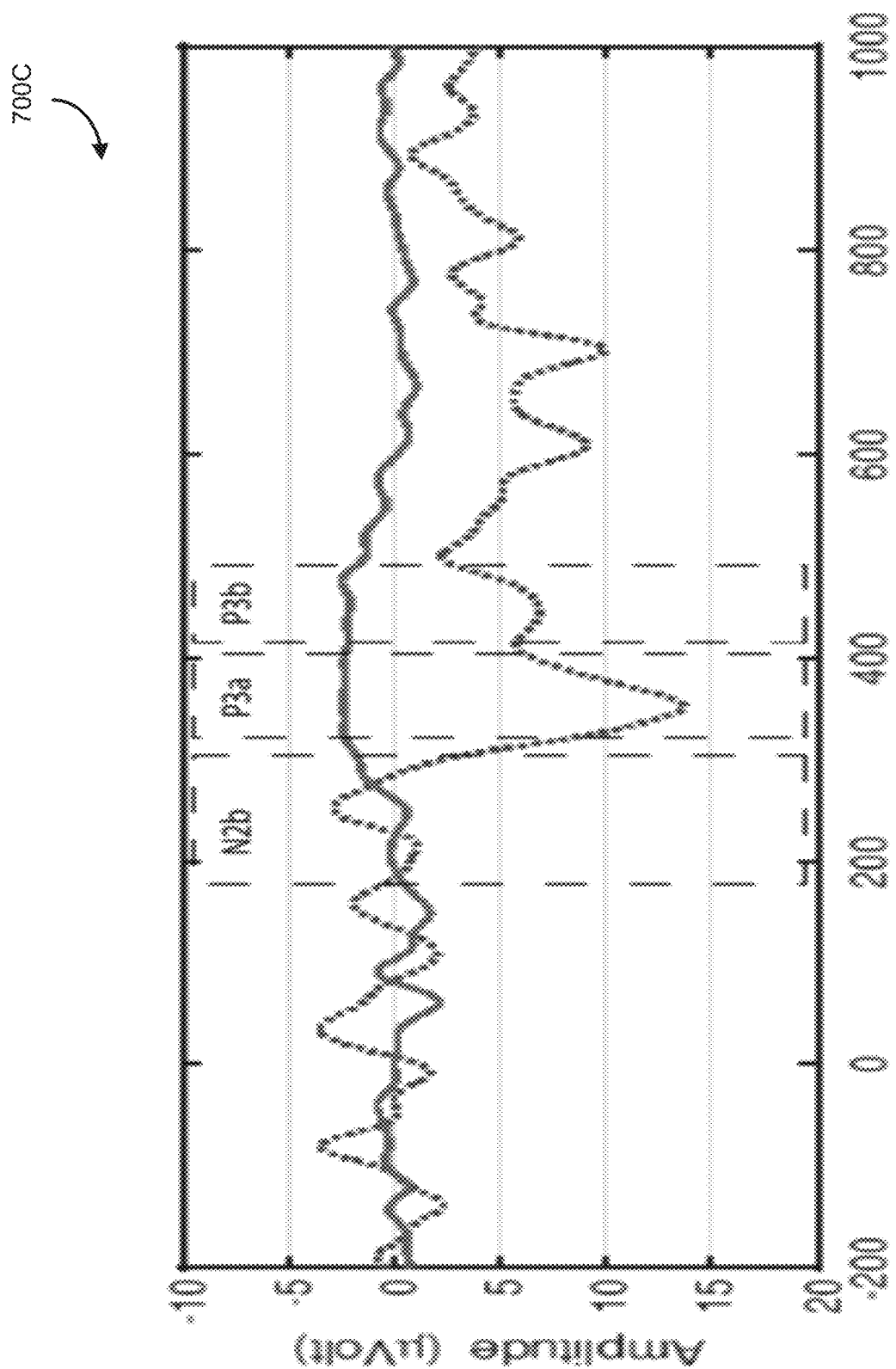

FIG. 7C includes the example graph 700C, showing example N2b, P3a, and P3b responses showing amplitude charted against time.

Figure 7D:
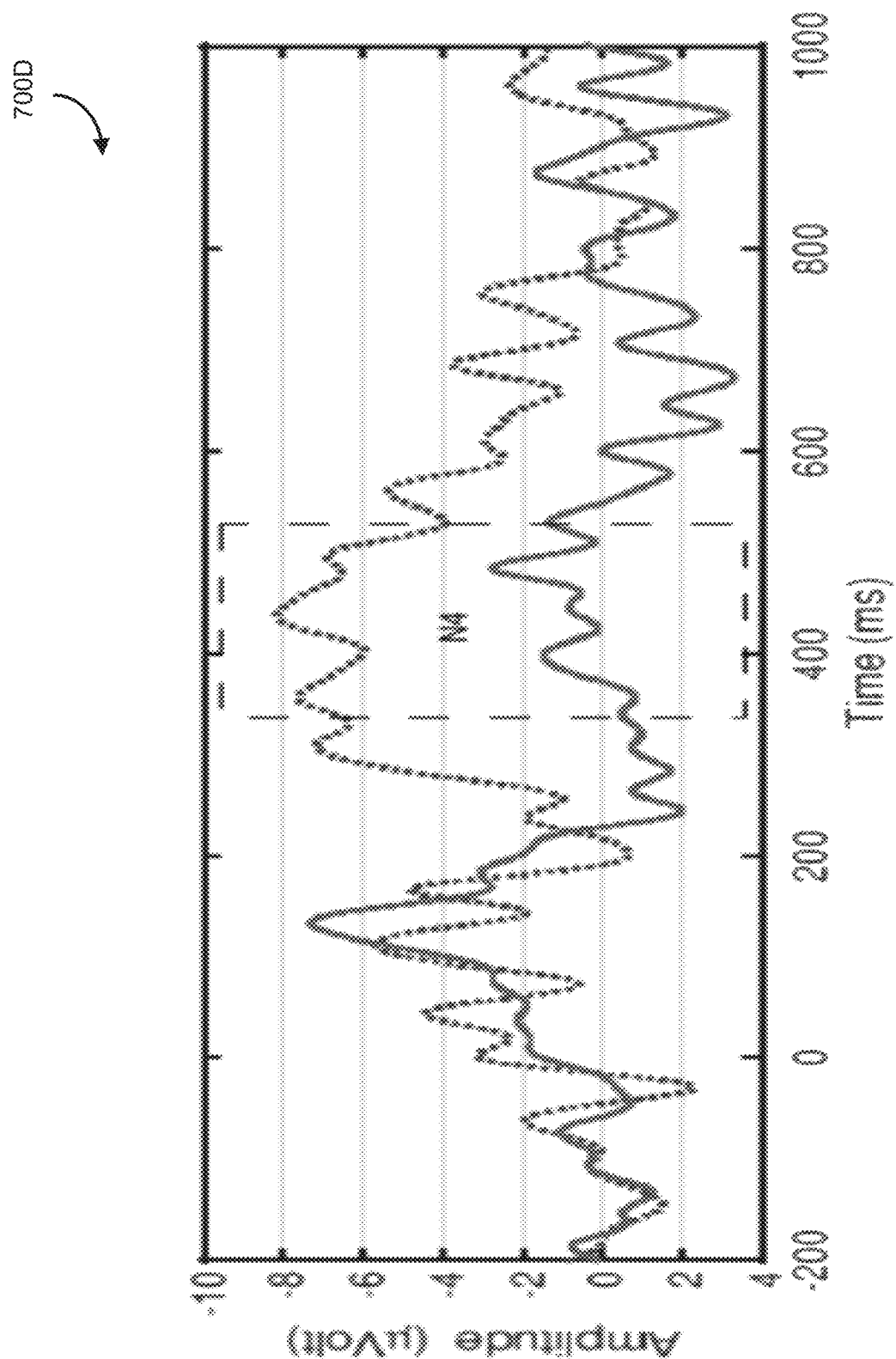

FIG. 7D includes the example graph 700D, showing an example N4 response showing amplitude charted against time.

Figure 8A:
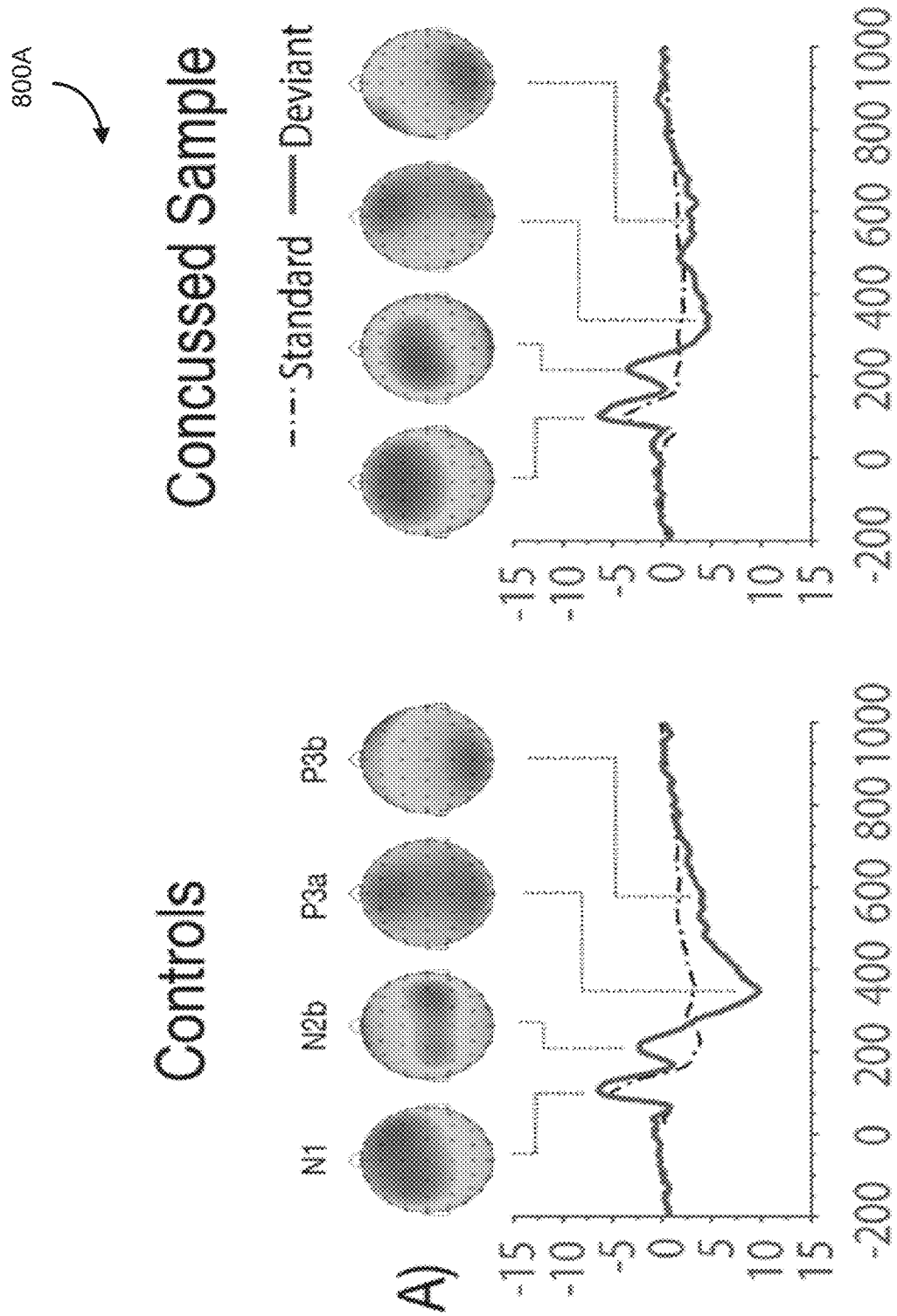
FIG. 8A, FIG. 8B, and FIG. 8C are example interface screens comparing brainwave patterns of a patient compared to a concussed control group, according to some embodiments.
Figure 8B:
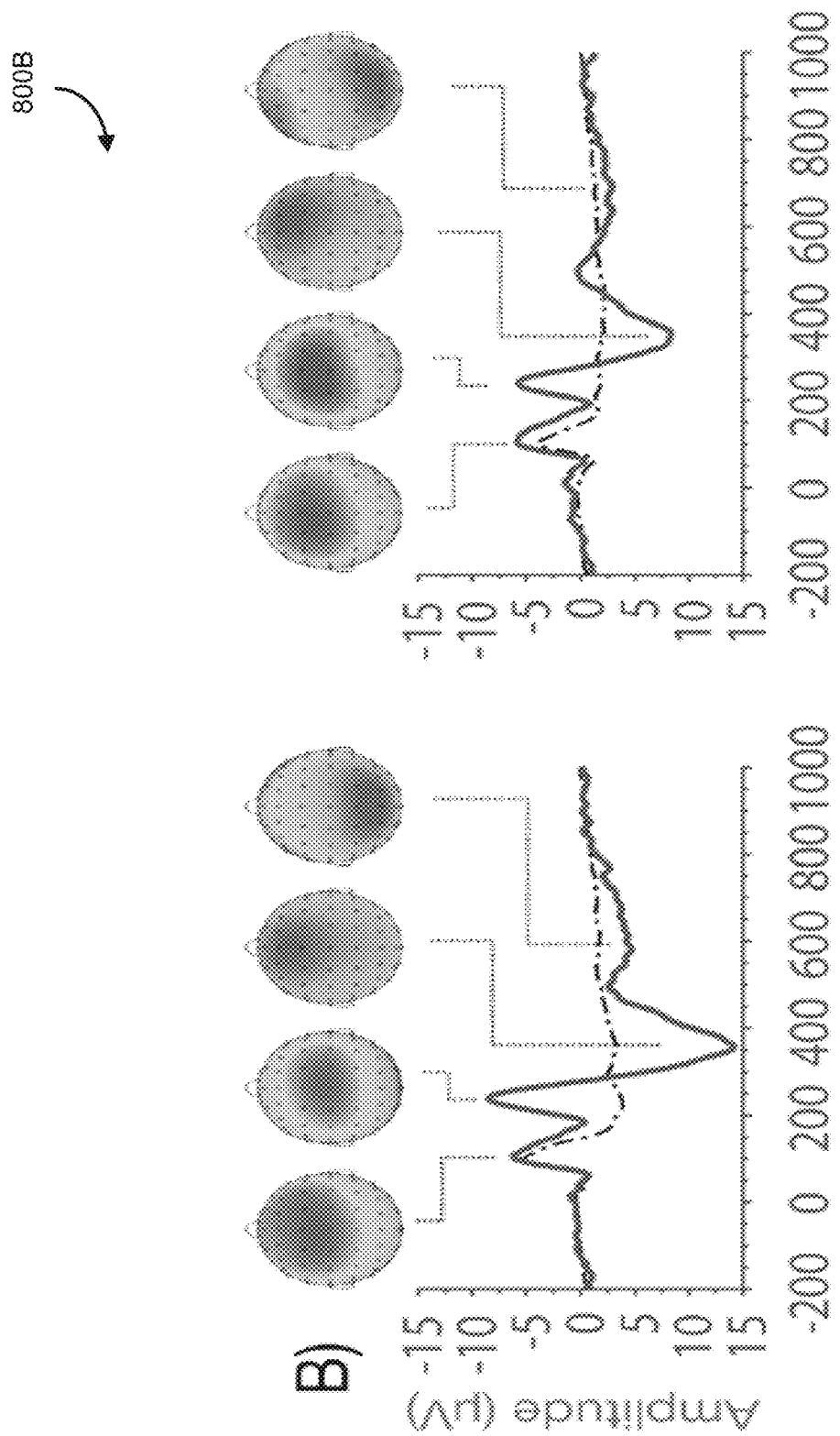
Figure 8C:
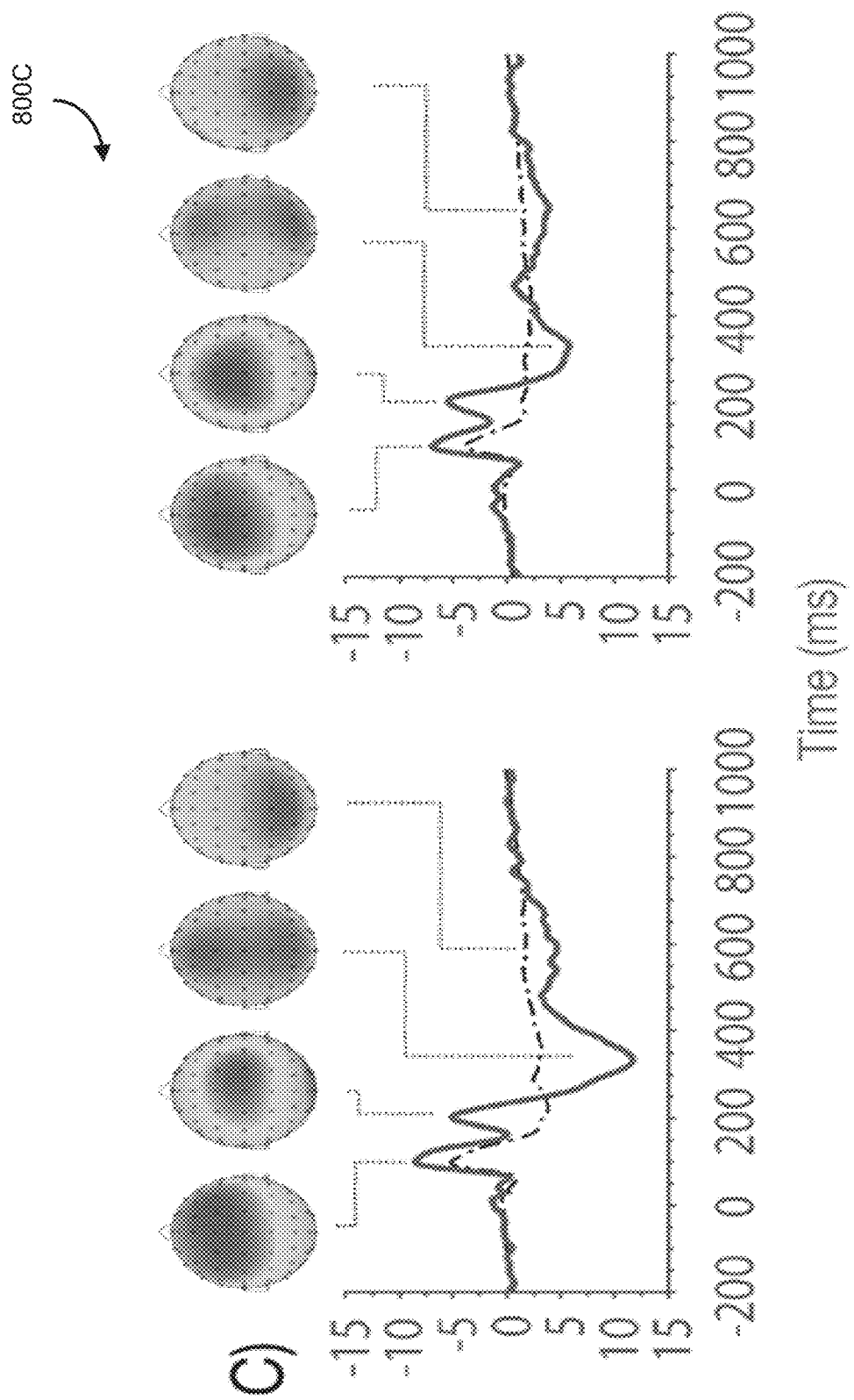

FIG. 8A, FIG. 8B, and FIG. 8C are example interface screens comparing brainwave patterns of a patient compared to a concussed control group, according to some embodiments. FIGS. 8A-8C illustrates topographical mapping generated throughout waveform data collection. Areas of the brain 'light up' at the time of an ERP response. Although one may see irregular responses in waveforms, one may not see irregularities on the topographical maps or vice versa. Therefore, topographical maps confirm the elicitation of an ERP.

FIGS. 8A-C shows grand-averaged P300 protocol waveforms and their respective scalp distributions recorded at Cz, evoked by target stimuli, for each group (Controls Left, Concussed person, Right). (A) 800A: N1, N2b, P3a, and P3b components evoked in the Frequency condition. (B) 800B: N1, N2b, P3a, and P3b components evoked in the Duration condition. (C) 800C: N1, N2b, P3a, and P3b components evoked in the Intensity condition.

Three different deviants (frequency/pitch, duration, intensity/loudness) were presented to different populations, as the different populations seem to respond differently to the different deviants:

P3as are fronto central and positive—darker grey regions.
P3bs are centro-parietal and positive—darker grey regions.

Examining the waveforms for the Controls, a clear N1 response is seen to stimulus onset with a typical frontocentral distribution (FIG. 8A, 8B, 8C); similar characteristics are observed in the concussed group. The following N2b component exhibits a characteristic central distribution with minor representation at frontal sites (FIG. 8A, 8B, 8C).

These waveform morphological features are also seen in the concussed group, although the N2b has increased frontal representation in the concussed group that is seen in response to Duration (FIG. 8B) and Intensity (FIG. 8C) deviants, in particular.

However, the comparative topographical maps for the P300 exhibit clear differences in the development and distribution of the P300 in response to each deviant stimulus type. In controls, the P3a element of the P300 exhibits a frontal distribution that extends in an anterior-posterior manner as far back as the occipito-parietal sites for Frequency and Intensity deviants (FIG. 8A, 8C) but shows only a frontocentral distribution for Duration deviants (FIG. 8B).

These distributional effects suggest a combinatorial P3a and b in this waveform. The topographical maps for the concussed group show a similar anterior-posterior distribution; however, a fairly striking left-sided absence of a response resulting in an unusual right asymmetry of the response is apparent across all types of deviants (FIG. 8A, 8B, 8C). The P3b occurring quite late for both Controls and concussed groups exhibits a parietal distribution that is apparent and similar in both groups.

The most striking feature of these waveforms is the near 50% reduction in P300 amplitude (both P3a and P3b) in the concussed group across all conditions (FIGS. 8A-8C) compared to Controls and the smaller but still notably reduced N2b amplitude again in the concussed group.

Statistical analysis provided confirmatory support for observations (Table 1, below). Group differences were not observed for either the latency or amplitude of the N1. However, N2b amplitudes proved to be significantly smaller in the concussed group compared to the control sample ($F(1, 35)=5.08$, $P<0.05$). Additionally, there was an interaction of Group X Condition for the N2b amplitudes ($F (2, 70)=4.91$, $P<0.05$) that post hoc analysis revealed was attributable to the much smaller amplitudes to Duration deviants in the concussed group compared to Controls ($F (1, 35)=14.38$, $P<0.01$). There was a main effect of Group such that the P3a amplitudes in the concussed group were significantly smaller than those exhibited in the Control sample ($F (1, 35)=6.34$, $P<0.05$). In addition, delayed response latencies were found for the P3b in the concussed group compared to Controls ($F (1, 35)=15.32$, $P<0.01$). Lastly, it was found that a main effect of group on P3b amplitude ($F (1, 35)=8.08$, $P<0.01$) where the concussed group exhibited a reduction in P3b amplitude compared to healthy control participants.

The abnormalities found in two different levels of attention as manifested by the P300 and MMN in this example indicate potential issues related to concussions. Increased latencies of the P300 may be a reflection of greater difficulties in allocating attentional resources for memory processing, and latency delays of the P3b component can be interpreted as indicative of slower cognitive processing speeds. The N2b is sensitive to stimulus deviance from an on-going sequence only when stimuli are being attended to; a characteristic demonstrating that the N2b requires and reflects conscious attention.

The decrease in N2b amplitude may reflect a deficit in the processing capacity of information contained in a stimulus. With the addition of the MMN protocol, the system adds a level of understanding to the cognitive consequences of concussions. As noted above, the MMN is associated with a level of "pre-attentive" processing that is elicited independently of conscious attention while still requiring the individual to be in a conscious state in addition, exclusively within the MMN protocol, the study results noted above demonstrated a significant reduction in N1 amplitude. The N1 is a pre-attentive ERP linked to the auditory cortex that has been found to be sensitive to loudness, frequency, and sound onset. The significant decrease in N1 amplitude may suggest difficulties in auditory processing.

Figure 9:
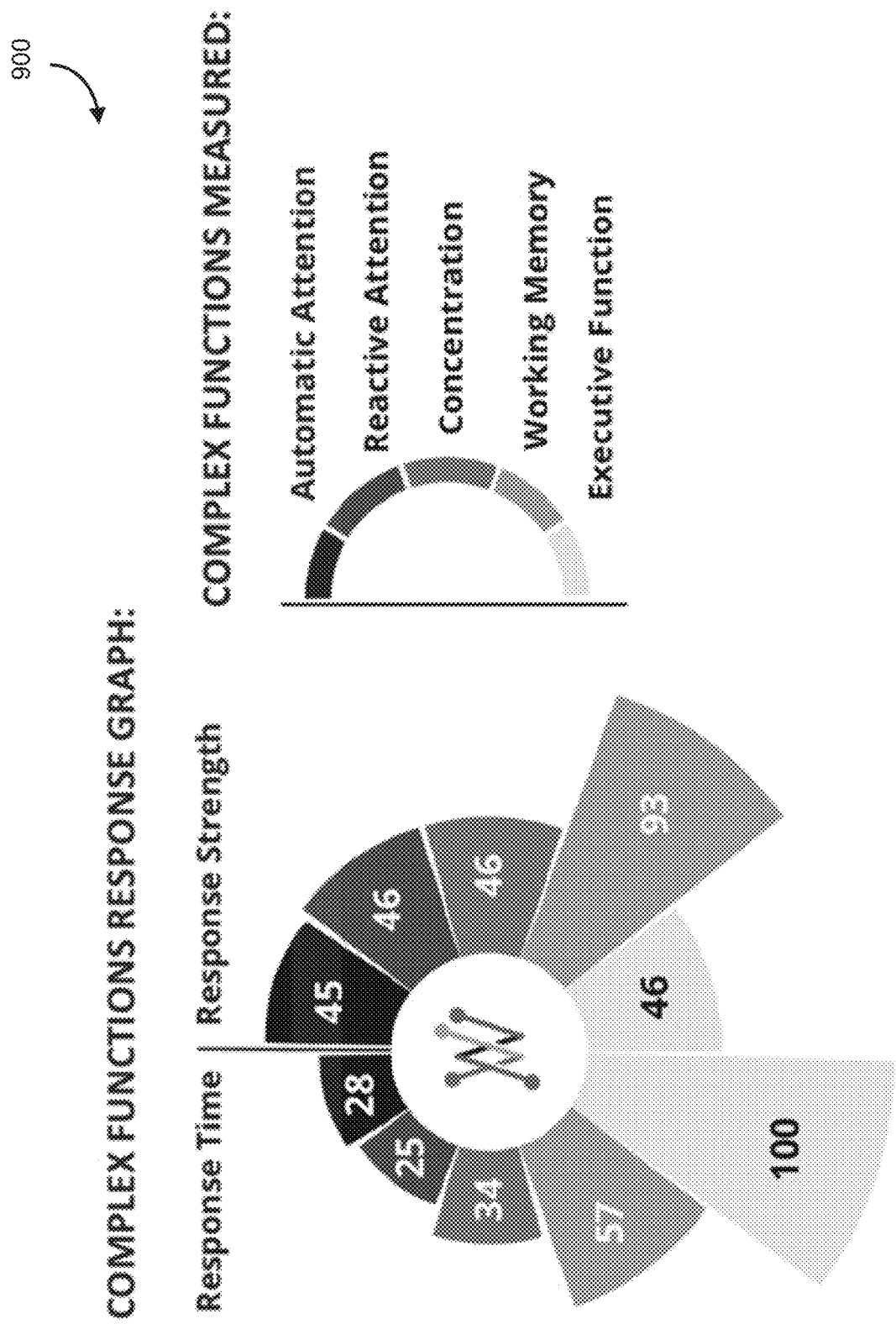
FIG. 9 shows example graphical results of a patient's brain function data from a cognitive health assessment report

FIG. 9 shows a graphical user interface 900 including example results from a cognitive health assessment report.

The patient's complex function EEG data is illustrated on a Percentile Value Scale. The graphical results present a complete view of a patient's performance across complex cognitive function categories that can be compared numerically to healthy controls. Each cognitive function is presented with a unique color and reports the neurophysiological performance of the patient as detected in response time (left semicircle) and response strength (right semicircle).

Percentile Value Scale: Each patient is compared to a reference database of neurophysiological brain responses. A numeric value is used to represent the patient responses relative to healthy controls on a scale from 1 to 100.

There can be three categories of performance, for example:

75-100: indicates a NORMAL response 25-75: indicates a MODERATE DEFICIENCY below 25: indicates a SEVERE DEFICIENCY Once EEG data is collected during a patient's cognitive health assessment, it is statistically analyzed through the system's analysis software.

An example of the steps involved include the following: The 64 electrode scalp positions on the head are divided into 20 segregated Regions of Interest (ROIs), with 3 to 6 electrodes per region.

Regions are created by clustering electrodes from left (L), midline (M), and right (R) positions with frontal (F), central (C), and parietal (P) positions. Of those 20 ROIs, 9 are selected and subsequently grouped into 3 independent scalp sectors: Frontal (R-F, M-F, L-F), Central (R-C, M-C, L-C), and Parietal (R-P, M-P, L-P).

Statistical analyses are performed for both amplitude and latency using mixed-effects analysis of variance (ANOVAs) with an alpha level of $P<0.05$. Degrees of freedom are corrected using the more conservative Greenhouse-Geisser estimates of epsilon to ensure avoidance of Type 1 errors. EEG analyses are conducted on the peak amplitude (defined as the average amplitude within a time-window of −50 ms to +50 ms around the detected peak) and latency (defined from stimulus onset to the detected peak) of ERP components for each condition (Standard, Frequency, and Duration) within ROIs where these specific components are found to be maximal.

These statistical analyses are utilized to determine differences in amplitude and latency of different ERP components of each test within the cognitive health assessment. These statistical analyses are utilized to determine differences in amplitude and latency of different ERP components of each test between an individual patient and control groups.

These results are then processed by an algorithm in the software to change the numerical representations into the Percentile Value Scale as shown on the Complex Functions Response Graph. Initial and follow-up assessment comparative analyses are conducted independently and in the case of the follow-up assessment, then further compared to track differences in ERP responses between the two (or more) test sessions to track a patient's cognitive progression.

Table 1, below, is a non-limiting example reference illustrating between group differences of amplitude and latency for the N1 and MMN within the MMN Protocol, as well as the N1, N2b, P3a, and P3b within the P300 Protocol after Greenhouse-Geisser corrections for multiple comparisons were applied. Other values are possible in respect of different demographics, and the values below are shown for illustration only.

TABLE 1

| MMN Protocol | | | | P300 Protocol | | | | | | | |
|---|---|---|---|---|---|---|---|---|---|---|---|
| N1 Amplitude | | | | N1 Amplitude | | | | P3a Amplitude | | | |
| Effect | df | F | P | Effect | df | F | P | Effect | df | F | P |
| Group | 35 | 5.74 | <0.05' | Group | 35 | 1.88 | >0.05 | Group | 35 | 6.34 | <0.05' |
| Group: Condition | 105 | 2.19 | >0.05 | Group: Condition | 105 | 105 | >0.05 | Group: Condition | 70 | 0.16 | >0.05 |
| Group: Region | 280 | 2.96 | >0.05 | Group: Region | 280 | 280 | >0.05 | Group: Region | 280 | 1.15 | >0.05 |
| N1 Latency | | | | N1 Latency | | | | P3a Latency | | | |
| Effect | df | F | P | Effect | df | F | P | Effect | df | F | P |
| Group | 35 | 0.8 | >0.05 | Group | 35 | 0.12 | >0.05 | Group | 35 | 1.24 | >0.05 |
| Group: Condition | 105 | 0.79 | >0.05 | Group: Condition | 105 | 0.25 | >0.05 | Group: Condition | 70 | 1.01 | >0.05 |
| Group: Region | 280 | 0.26 | >0.05 | Group: Region | 280 | 0.83 | >0.05 | Group: Region | 280 | 0.92 | >0.05 |
| MMN Amplitude | | | | N2b Amplitude | | | | P3b Amplitude | | | |
| Effect | df | F | P | Effect | df | F | P | Effect | df | F | P |
| Group | 35 | 10.01 | <0.01" | Group | 35 | 5.08 | <0.05' | Group | 35 | 8.08 | <0.01" |
| Group: Condition | 70 | 5.98 | <0.03" | Group: Condition | 70 | 4.91 | <0.05' | Group: Condition | 70 | 1.06 | >0.05 |
| Group: Region | 280 | 1.59 | >0.05 | Group: Region | 280 | 0.42 | >0.05 | Group: Region | 280 | 1.43 | >0.05 |
| MMN Latency | | | | N2b Latency | | | | P3b Latency | | | |
| Effect | df | F | P | Effect | df | F | P | Effect | df | F | P |
| Group | 35 | 0.85 | >0.05 | Group | 35 | 0.75 | >0.05 | Group | 35 | 15.32 | <0.01" |
| Group: Condition | 70 | 1.24 | >0.05 | Group: Condition | 70 | 0.1 | >0.05 | Group: Condition | 70 | 3.28 | >0.05 |
| Group: Region | 280 | 0.42 | >0.05 | Group: Region | 280 | 0.85 | >0.05 | Group: Region | 280 | 0.22 | >0.05 |

Note:
":" denotes an Interaction.
'Indicates Significance Between Groups <0.05.
"Indicates Significance Between Groups <0.01.

The differences in the amplitude and latency of different ERP components of each test between an individual patient and control groups are used to establish a graphical visual element size/position factor that is based on the percentile value scale. The numeric value that was used to represent the patient responses relative to healthy controls on a scale from 1 to 100 is used to modify the sizing of a visual element representing a normalized score for a particular category.

In some embodiments, the visual element is a slice of an exploded pie chart (e.g., the chart shown on the left). The factoring can be based on a radius of the graphical representation, modifying the radius based on a percentage from 0-100%—for example, executive function at 100 has a full radius, while the other complex functions being measured have reduced radii. Other visual characteristics may also be controlled, such as the color, opacity, tint, saturation, of the visual element. In another embodiment, the visual element is a bar chart. In some embodiments, to reduce an overall computational load by the device displaying the graphical representation, the data structure transmitted to the device includes pre-generated size factor scores, generated by a backend server having more computational resources.

Figure 10:
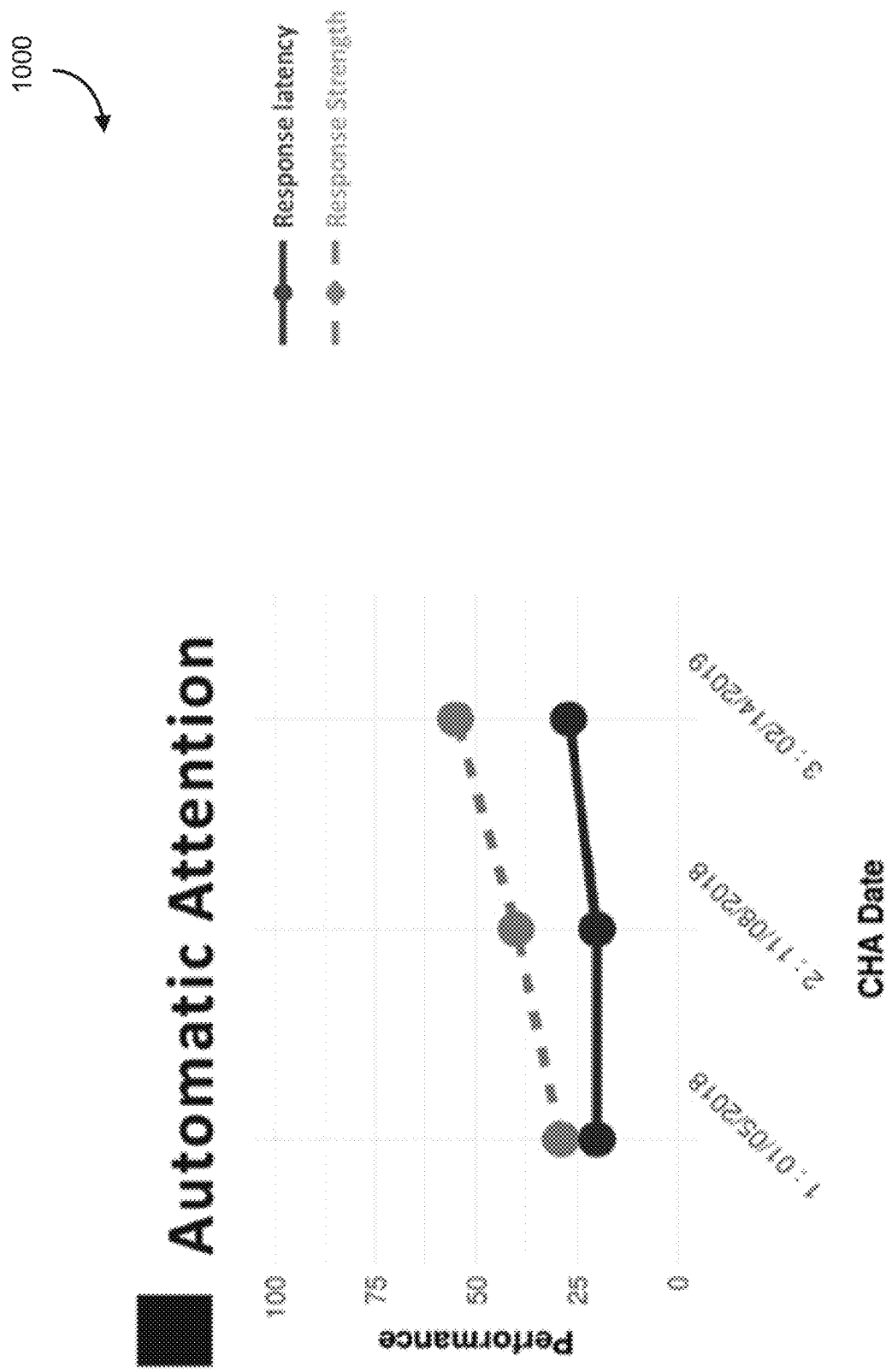
FIG. 10 shows example recovery progress tracker from a cognitive health assessment report through repeat testing.

FIG. 10 is a diagram showing an example recovery progress tracker 1000 from a cognitive health assessment report through repeat testing. A different type of visual element is presented that shows changes over a period of time.

Figure 11:
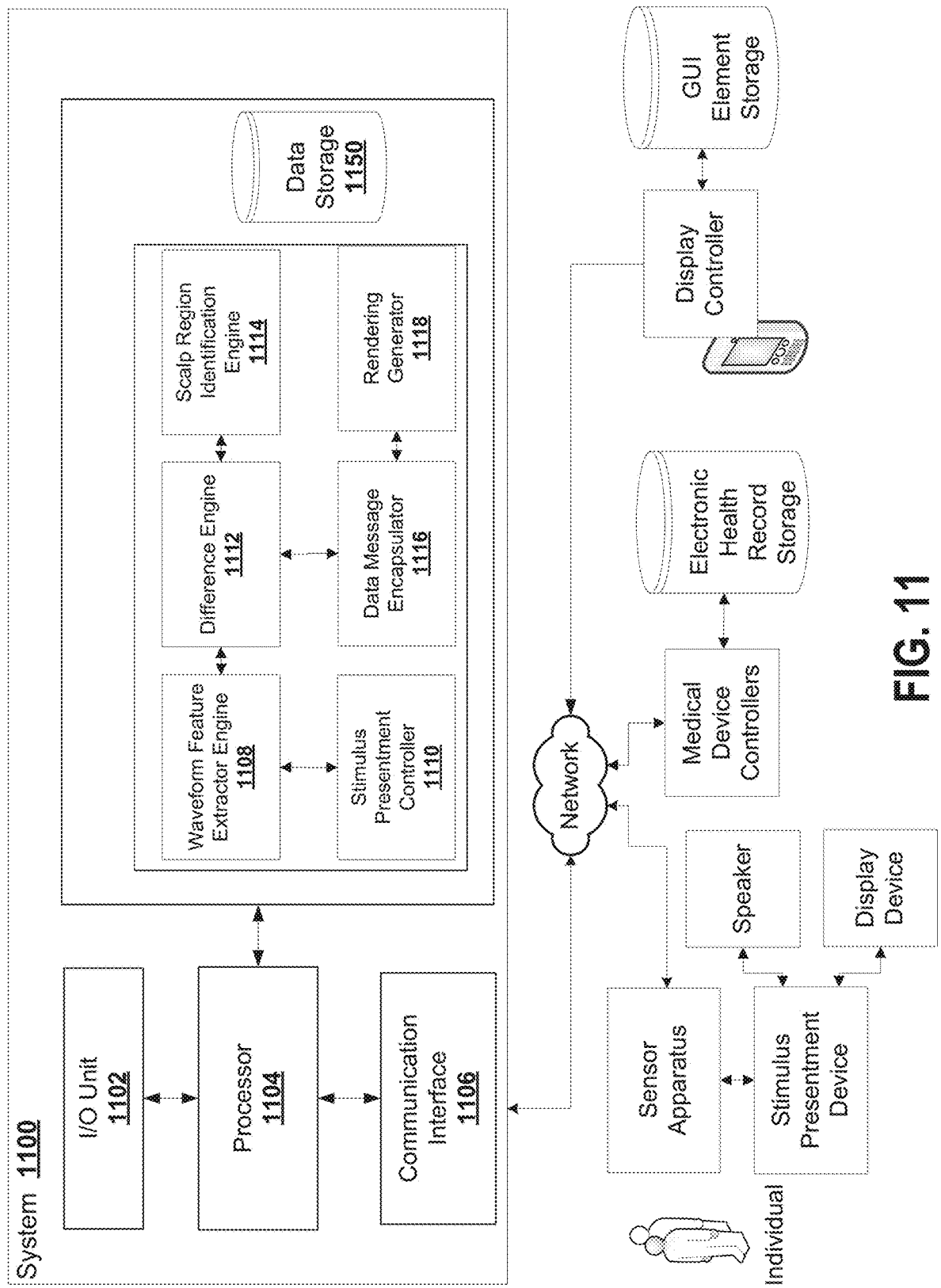
FIG. 11 is a block schematic of an example computing device, according to some embodiments.

FIG. 11 is a block schematic of an example computing device 1100, according to some embodiments. The components shown are electronic computing components and can include a combination of hardware and software. Electrical circuits are specially programmed using machine-interpretable instruction sets and the schematics shown are non-limiting examples. For example, other, alternate, or different components are possible.

The device 1100 includes an interface unit 1102, which receives one or more data streams from the sensor apparatus and controls data transmissions to the stimulus presentment device, or downstream computing devices, such as medical device controllers, electronic health record data storages, and display controllers that control one or more graphical user interfaces (e.g., a report engine). The interface unit 1102 can also receive various commands from an operator, such as initiate assessment, an indication of type of individual being assessed, among others.

The processor 1104 can include microprocessors, systems on a chip, and field programmable gate arrays. The processor 1104 executes machine interpretable instruction sets which configure the processor to perform steps of a method for health assessment, and in some embodiments, the method further includes medical device control, display rendering of a graphical user interface, or appending data to electronic health record storage elements. The processor 1104 can include a central processing unit and can be an integrated circuit, and can include computing elements, such as a digital clock, one or more data registers, among others.

The communication interface 1106 is interoperable with a network to receive, transmit and process data packets through the network. The communication interface 1106 can include a wireless connection, a cellular connection, a satellite connection, or a wired connection.

The processor 1104 includes instruction sets which include computer programs and software which are directed to process the data sets using a waveform feature extractor engine 1108. Steps of the assessment are generated by stimulus presentment controller 1110, and provided as instruction sets for controlling the stimulus presentment device. As described in various embodiments, the stimulus presentment controller 1110 controls the presentment of tactile, vibratory, audible, visible, and/or olfactory stimuli, which can include aberrant or deviant versions of the same. The stimulus presentment controller 1110 is configured to generate sustained stimuli overlaid with deviant stimuli, and in some embodiments, repetitive stimuli, depending on the particular brainwave pattern being tracked. The stimulus presentment controller 1110 can be connected, for example, to a speaker and/or a display device. The various types of stimuli, including standard and deviant versions thereof, can be retrieved from a data storage 1150.

The difference engine 1112 is configured to generate metrics from the received signals, for example, by comparing the metrics against demographic controls from a population-level analysis, indicating, for example, how the individual responds to various stimuli and whether there may be potential issues in relation to at least one of the metrics being evaluated. In some embodiments, the scalp region identification engine 1114 segregates the signals received from the sensor apparatus and conducts the differencing analysis to assess scalp-region related differences from the control, providing greater granularity and resolution to the metrics. For example, there may be reduced brain functionality or modified functionality isolated to specific brain regions as identified through the scalp positioning of the electrodes at various regions of interest.

The data message encapsulator 1116 is configured to generate instruction messages which can be data structures including various fields for updating electronic health records (e.g., encapsulated HL7 schema based messages) or JSON/XML files that modify parameters of medical device operation (e.g., modify a polling rate or an alert/alarm threshold, this patient is potentially not comatose) or notification/alert generation thereof.

The rendering generator 1118 is configured to generate one or more graphical user interface visual elements based on the determined metrics from the brain assessment techniques described in various embodiments herein. The graphical user interface visual elements are encapsulated as data message elements which can be transmitted to a display controller and stored on a graphical user interface element storage. The graphical user interface can be invoked by the computing device (e.g., a doctor or a nurse's work station) such that the rendering can be generated as a static image or as a dynamically generated set of user interface elements. As noted in embodiments herein, the encapsulated message can include metric data which can be transformed by the display controller into visual characteristic values for the user interface elements, or in other embodiments, the visual characteristic values are pre-processed and transmitted to the display controller (e.g., where the display controller has limited computational functionality).

FIG. 12 is a method diagram 1200 of an example process, according to some embodiments. In FIG. 12, a method for generating data sets representative of potential cognitive activity of a patient is shown. The steps shown are examples and alternate, different, less, more steps are possible. For example, as noted in some embodiments, a partial battery of tests may be suitable in certain situations.

The method operates on a computing system 1100 for generating data sets representative of potential cognitive activity of a patient, the computing system including at least one processor and computer readable memory, the computing system comprising a sensor apparatus connected to one or more electrodes coupled to the patient's head, the one or more electrodes recording brainwave (EEG) data of the patient in respect of a brain of the patient; a stimulus presentation mechanism coupled to one or more sensory output devices, the stimulus presentation mechanism generating a series of programmed stimuli to the patient while the sensor apparatus records the brainwave data of the patient as the patient receives the series of programmed stimuli; and a waveform feature extractor processing engine configured to process the brainwave data of the patient to extract waveform features, the waveform features including at least one or more N1, P2, N400, MMN, P300 (P3a/P3b), and N2b responses.

The system uses a sensor apparatus connected to one or more electrodes coupled to the patient's head, the one or more electrodes recording brainwave (EEG) data of the patient in respect of a brain of the patient, a portion of brainwave data of the patient during a first resting period during which no stimulus is being presented to the patient.

Stimuli, including repeated stimuli and deviant/modified stimuli, can be sourced from a data storage element, or in some embodiments, transformed based on the standard stimuli (e.g., modification of pitch or duration).

At 1202, the processor executes a process for controlling a stimulus presentation mechanism to present a repeated auditory tone or visual image presentation to the patient; and tracking, on a processor configured for monitoring data received from the sensor apparatus the one or more N1 and P2 responses to auditory tones or words to measure the brain's processing of auditory stimuli or N1 and P2 responses to visual stimuli to measure the brain's processing of visual stimuli.

At 1204, the processor executes a process for controlling the stimulus presentation mechanism to present one or more auditory or visual phrases each including one or more nonsensical, or otherwise inaccurate or unexpected portions of a sentence to the patient and tracking, by the processor: the one or more N400 responses recorded in one or more waveform features during or proximate to the presentation of one or more nonsensical portions of a sentence to measure the brain's ability to process word and phrase meanings, sentence grammar and discourse.

At 1206, the processor executes a process for controlling the stimulus presentation mechanism to present one or more incongruous, unexpected or otherwise surprising words or sentences within a language context; and tracking, by the processor the one or more N400 responses recorded in one or more waveform features during or proximate to the presentation of one or more incongruous, unexpected or otherwise surprising words or sentences pairings to track the brain's ability to process word and phrase meanings, and vocabulary recognition.

At 1208, the processor executes a process for controlling the stimulus presentation mechanism to present repeated tones or visuals intermixed with deviant tones or visuals while presented in concert with a constant tone or visual; and tracking, by the processor:

the one or more MMN responses recorded in one or more waveform features during or proximate to the presentation of the one or more deviant tones or visuals to track the brain's ability to respond to environmental changes that are not actively attended.

At 1210, the processor executes a process for controlling the stimulus presentation mechanism to present repeated tones or visuals intermixed with deviant tones or visuals and tracking, by the processor: the one or more P3a responses recorded in one or more waveform features during or proximate to the presentation of one or more deviant tones or visuals to track the brain's ability to respond to stimulus deviance.

At 1212, the processor executes a process for controlling the stimulus presentation mechanism to present repeated tones or visuals intermixed with deviant tones or visuals while the patient has been instructed to actively recognize or respond to the deviant tones or visuals and tracking, by the processor: the one or more P3b responses recorded in one or more waveform features during or proximate to the presentation of one or more deviant tones or visuals to track the brain's ability to focus one's attention on a task.

At 1214, the processor executes a process for controlling the stimulus presentation mechanism to present complex visual or auditory pattern stimuli, at least one of which are repeated throughout the sequence while the patient has been instructed to actively recognize or respond to the repeated visuals or auditory tones or patterns and tracking, by the processor: the one or more P3b responses recorded in one or more waveform features during or proximate to the presentation of one or more repeated tones or visuals to track the brain's ability to temporarily hold information available for processing.

At 1206, the processor executes a process for controlling the stimulus presentation mechanism to present complex visual or auditory pattern stimuli, some of which are repeated throughout the sequence while the patient has been instructed to actively ignore specific visuals or auditory tones or patterns, and recognize or respond to alternate repeated visuals or auditory tones or patterns and tracking, by the processor the one or more N2b responses recorded in one or more waveform features during or proximate to the presentation of one or more repeated tones or visuals and reaction to one or more repeated tones or visuals to track the brain's ability to work through complex processes to enable complex behaviour.

The processor is configured for processing the data sets to identify one or more differences in the N1, P2, N400, MMN, P300 (P3a/P3b), N2b responses recorded in the one or more waveform features during the presentation of the repeated auditory tone or visual image presentation to the patient and during the presentation of the repeated auditory tone or visual image intermixed with the deviants, and the one or more P3b responses recorded in one or more waveform features in response to complex visual pattern stimuli, some of which are repeated throughout the sequence.

The processor then generates a data set based on the extracted waveform features, the data set including data fields corresponding to at least one of an automatic attention metric based at least on the differences in the one or more MMN responses, a reactive attention metric based at least on the differences in the one or more P3a responses, a concentration metric the differences in the one or more P3b responses, a working memory metric based at least the differences in the one or more P3a responses, or an executive function metric based at least on the differences in the one or more N2b responses.

In some embodiments, the tool is a standalone, special purpose machine that is adapted for use in a clinical setting. The special purpose machine may have specialized software and hardware, such as optimized integrated circuits or field programmable gate arrays. For example, the tool may be provided on a medical cart, coupled to a patient (e.g., following a concussion or a comatose patient), and the cognitive health assessments are measured as stimuli are presented (e.g., sound tones, vibrations, visual stimuli), or between when stimuli are presented. These stimuli are presented even to patients who are otherwise unresponsive (individuals with locked in syndrome, etc.). The tool includes EEG hardware, computer processors, and software that are specially configured in relation to performing the above tests. Stimuli and acquisition software are adapted based on the techniques described above, including statistical analysis and measurements, which responsive to the measurements, are used in generating decision support interfaces.

It will be appreciated that components exemplified herein that executes instructions that include or otherwise have access to computer readable media such as storage media, computer storage media, or data storage devices (removable and/or non-removable) such as, for example, magnetic disks, optical disks, tape, among others. Computer storage media includes volatile and non-volatile, removable and non-removable media implemented in any method or technology for storage of information, such as computer readable instructions, data structures, program modules, or other data.

Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or media which can be used to store the desired information and which can be accessed by an application, module, or both. Computer storage media may be part of the mobile device, tracking module, object tracking application, etc., or accessible or connectable thereto. Applications herein described are implemented using computer readable/ executable instructions that may be stored or otherwise held by such computer readable media.

Thus, alterations, modifications and variations can be affected to the particular embodiments by those of skill in the art without departing from the scope of this disclosure.

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made.

Except to the extent explicitly stated or inherent within the processes described, including any optional steps or components thereof, no required order, sequence, or combination is intended or implied. As will be understood by those skilled in the relevant arts, with respect to both processes and any systems, devices, etc., described herein, a wide range of variations is possible, and even advantageous, in various circumstances.

What is claimed is:

1. A computing system for automatically generating a cognitive health assessment report utilizing data sets representative of potential cognitive activity of a patient, the computing system including at least one processor and computer readable memory, the computing system comprising:
a sensor apparatus connected to one or more electrodes configured to be coupled to the patient's head, the one or more electrodes recording brainwave (EEG) data of the patient in respect of a brain of the patient;

a stimulus presentation mechanism coupled to one or more sensory output devices, the stimulus presentation mechanism generating a series of programmed stimuli to the patient while the sensor apparatus records the brainwave data of the patient as the patient receives the series of programmed stimuli;

a waveform feature extractor processing engine configured to process the brainwave data of the patient to extract one or more waveform features, the one or more waveform features including at least one or more N1, P2, N400, MMN, P300 (P3a/P3b), and N2b responses present in the brainwave data; and a processor configured to:
record, using the sensor apparatus, a portion of brainwave data of the patient during a resting period during which no stimulus is being presented to the patient;

control the stimulus presentation mechanism to present repeated auditory tones or visual images to the patient;

control the waveform feature extractor to track:
one or more N1 and P2 responses to the repeated auditory tones or visual images to measure the brain's processing of auditory stimuli or to measure the brain's processing of visual stimuli;

control the stimulus presentation mechanism to present one or more auditory or visual phrases each including one or more nonsensical, or otherwise inaccurate or unexpected portions of a sentence to the patient;

control the waveform feature extractor to track:
one or more N400 responses present in the brainwave data during the presentation of the one or more nonsensical, or otherwise inaccurate or unexpected portions of the sentence to measure the brain's ability to process word and phrase meanings, sentence grammar and discourse;

control the stimulus presentation mechanism to present one or more incongruous, unexpected or otherwise surprising words or sentence pairings within a language context;

control the waveform feature extractor to track:
one or more N400 responses present in the brainwave data during the presentation of the one or more incongruous, unexpected or otherwise surprising words or sentence pairings to track the brain's ability to process word and phrase meanings, and vocabulary recognition;

control the stimulus presentation mechanism to present a first set of repeated tones or visuals intermixed with a first set of deviant tones or visuals in concert with a constant tone or visual; and control the waveform feature extractor to track:
one or more MMN responses present in the brainwave data during the presentation of the first set of deviant tones or visuals to track the brain's ability to respond to environmental changes that are not actively attended;

control the stimulus presentation mechanism to present a second set of repeated tones or visuals intermixed with a second set of deviant tones or visuals;

control the waveform feature extractor to track:
one or more P3a responses present in the brainwave data during the presentation of the second set of deviant tones or visuals to track the brain's ability to respond to stimulus deviance;

control the stimulus presentation mechanism to present the second set of repeated tones or visuals intermixed with the second set of deviant tones or visuals and to automatically present instructions rendered on a computer screen or generate audible instructions instructing the patient to actively recognize or respond to the second set of deviant tones or visuals;

control the waveform feature extractor to track:
one or more P3b responses present in the brainwave data during the presentation of the second set of deviant tones or visuals to track the brain's ability to focus attention on a task;

control the stimulus presentation mechanism to present a first set of visual or auditory pattern stimuli, at least one stimuli of which are repeated throughout the first set of visual or auditory pattern stimuli and to automatically present instructions rendered on the computer screen or generate audible instructions instructing the patient to actively recognize or respond to the repeated stimuli in the first set of visual or auditory pattern stimuli;

control the waveform feature extractor to track:
one or more P3b responses present in the brainwave data during the presentation of the first set of visual or auditory pattern stimuli to temporarily hold information available for processing;

control the stimulus presentation mechanism to present a second set of visual or auditory pattern stimuli, at least one stimuli of which are repeated throughout the second set of visual or auditory pattern stimuli and to automatically present instructions rendered on the computer screen or generate audible instructions instructing the patient to actively ignore specific visuals or auditory tones or patterns, and recognize or respond to alternate repeated visuals or auditory tones or patterns in the second set of visual or auditory pattern stimuli;

control the waveform feature extractor to track:
one or more N2b responses present in the brainwave data during the presentation of the second set of visual or auditory pattern stimuli to track the brain's ability to work through complex processes to enable complex behaviour;

respective differences in amplitude or latency of the N1, P2, N400, MMN, P300 (p3a/P3b), and N2b responses relative to corresponding responses in a control group; and the one or more P3b responses;

determine at least one of an automatic attention value based at least on the differences in the one or more MMN responses, a reactive attention value based at least on the differences in the one or more P3a responses, a concentration value based on at least the differences in the one or more P3b responses, a working memory value based at least on the differences in the one or more P3a responses, or an executive function value based at least on the differences in the one or more N2b responses;

encapsulate as a data set into a data structure representing the cognitive health assessment report, the at least one of the automatic attention value, the reactive attention value, the concentration value, the working memory value, or the executive function value; and automatically generate and present, to an individual on a graphical user interface, the cognitive health assessment report generated based on the data set;

wherein the patient is elderly, disabled, diagnosed with a potential concussion or acquired brain injuries, is in an unresponsive state or is comatose.

2. The system of claim 1, wherein the one or more electrodes include a plurality of electrodes that are configured to be positioned within a plurality of segregated regions of interest, with at least one electrode per region of interest.

3. The system of claim 2, wherein the segregated regions of interests are further to establish three independent scalp sectors, a frontal sector, a central sector, and a third parietal sector, and wherein the one or more P3a responses are measured from the frontal sector and the central sector, and the one or more P3b responses are measured from the central sector and the parietal sector, wherein a distribution between the three independent scalp sectors is utilized in generating at least one of the reactive attention value, the concentration value, the working memory value or the executive function value; and, wherein the distribution between the three independent scalp sectors is utilized in rendering one or more graphical representations of the patient's brain in the automatically generated cognitive health assessment report.

4. The system of claim 1, wherein the differences for the one or more MMN responses and the one or more N1 responses are based on amplitude, and the differences for the one or more P300 responses is based on both amplitude and latency.

5. The system of claim 1, wherein the data set is transmitted to a display coupled to a computing device, and the processor is further configured to:
normalize and transform the determined values into one or more corresponding factors for modifying a visual element corresponding to each determined value,
wherein each factor modifies a size or color of a corresponding visual element.

6. The computing system of claim 1, wherein the patient is in an unresponsive state and the sensor apparatus is configured to record the brainwave data of the patient during one or more additional rest periods where the patient is not receiving the programmed stimuli.

7. The computing system of claim 1, wherein the processor is further configured to combine brainwave data of the patient during one or more additional rest periods where the patient is not receiving programmed stimuli with the brainwave data of the patient recorded relating to the presentation of the first or second set of visual or auditory pattern stimuli.

8. The computing system of claim 1, further comprising a display controller coupled to a display, the display controller configured to render a brain assessment interface including at least a representative mapping of the brain of the patient indicative of one or more areas of the brain that are activated responsive to the presentation of the first or second set of visual or auditory pattern stimuli.

9. The computing system of claim 1, further comprising a display controller coupled to a display, the display controller configured to render a brain assessment interface including at least a representative visual representation of the brain of the patient indicative of one or more areas of the brain that are activated during one or more rest periods between the presentation of the first and second set of visual or auditory pattern stimuli.

10. A method for automatically generating a cognitive health assessment report utilizing data sets representative of potential cognitive activity of a patient, the method comprising:
recording, using a sensor apparatus connected to one or more electrodes coupled to the patient's head, the one or more electrodes recording brainwave (EEG) data of the patient in respect of a brain of the patient, a portion of brainwave data of the patient during a first resting period during which no stimulus is being presented to the patient;
processing the brainwave data of the patient to extract one or more waveform features, the one or more waveform features including at least one or more N1, P2, N400, MMN, P300 (P3a/P3b), and N2b responses present in the brainwave data;
controlling a stimulus presentation mechanism to present repeated auditory tones or visual images to the patient;
tracking, on a processor configured for monitoring data received from the sensor apparatus:
one or more N1 and P2 responses to the repeated auditory tones or visual images to measure the brain's processing of auditory stimuli or to measure the brain's processing of visual stimuli;
controlling the stimulus presentation mechanism to present one or more auditory or visual phrases each including one or more nonsensical, or otherwise inaccurate or unexpected portions of a sentence to the patient;
tracking, by the processor:
one or more N400 responses present in the brainwave data during the presentation of the one or more nonsensical, or otherwise inaccurate or unexpected portions of the sentence to measure the brain's ability to process word and phrase meanings, sentence grammar and discourse;
controlling the stimulus presentation mechanism to present one or more incongruous, unexpected or otherwise surprising words or sentences within a language context;
tracking, by the processor:
one or more N400 responses present in the brainwave data during the presentation of the one or more incongruous, unexpected or otherwise surprising words or sentence pairings to track the brain's ability to process word and phrase meanings, and vocabulary recognition;
controlling the stimulus presentation mechanism to present a first set of repeated tones or visuals intermixed with a first set of deviant tones or visuals in concert with a constant tone or visual; and
tracking, by the processor:
one or more MMN responses present in the brainwave data during the presentation of the first set of one or more deviant tones or visuals to track the brain's ability to respond to environmental changes that are not actively attended;
controlling the stimulus presentation mechanism to present a second set of repeated tones or visuals intermixed with a second set of deviant tones or visuals;
tracking, by the processor:
one or more P3a responses present in the brainwave data during the presentation of the one or more deviant tones or visuals to track the brain's ability to respond to stimulus deviance;
controlling the stimulus presentation mechanism to present the second set of repeated tones or visuals intermixed with the second set of deviant tones or visuals and instructing the patient to actively recognize or respond to the second set of deviant tones or visuals;
tracking, by the processor:
one or more P3b responses present in the brainwave data during the presentation of the second set of deviant tones or visuals to track the brain's ability to focus one's attention on a task;

controlling the stimulus presentation mechanism to present a first set of visual or auditory pattern stimuli, at least one stimuli of which are repeated throughout instructing the patient to actively recognize or respond to the repeated stimuli in the first set of visual or auditory pattern stimuli;

tracking, by the processor:
one or more P3b responses present in the brainwave data during the presentation of first set of visual or auditory pattern stimuli to temporarily hold information available for processing;

controlling the stimulus presentation mechanism to present a second set of visual or auditory pattern stimuli, at least one stimuli of which are repeated throughout the second set of visual or auditory pattern stimuli and instructing the patient to actively ignore the specific visuals or auditory tones or patterns, and recognize or respond to the alternate repeated visuals or auditory tones or patterns in the second set of visual or auditory pattern stimuli;

tracking, by the processor:
one or more N2b responses present in the brainwave data during the presentation of the second set of visual or auditory pattern stimuli to track the brain's ability to work through complex processes to enable complex behaviour;
respective differences in amplitude or latency of the N1, P2, N400, MMN, P300 (P3a/P3b), and N2b responses relative to corresponding responses in a control group; and
the one or more P3b responses;

determining at least one of an automatic attention value based at least on the differences in the one or more MMN responses, a reactive attention value based at least on the differences in the one or more P3a responses, a concentration value based on the differences in the one or more P3b responses, a working memory value based at least on the differences in the one or more P3a responses, or an executive function value based at least on the differences in the one or more N2b responses;

encapsulating as a data set into a data structure representing the cognitive health assessment report, the at least one of the automatic attention value, the reactive attention value, the concentration value, the working memory value, or the executive function value; and automatically generating and presenting, to an individual on a graphical user interface, the cognitive health assessment report generated based on the data set;

wherein the patient is elderly, disabled, diagnosed with a potential concussion or acquired brain injuries, is in an unresponsive state or is comatose.

11. The method of claim 10, wherein the one or more electrodes coupled to the patient's head to record brainwave (EEG) data include a plurality of electrodes that are positioned within a plurality of segregated regions of interest, with at least one electrode per region of interest.

12. The method of claim 11, wherein the segregated regions of interests are further to establish three independent scalp sectors, a frontal sector, a central sector, and a third parietal sector, and wherein the one or more P3a responses are measured from the frontal sector and the central sector, and the one or more P3b responses are measured from the central sector and the parietal sector, wherein a distribution between the three independent scalp sectors is utilized in generating at least one of the reactive attention value, the concentration value, the working memory value or the executive function value; and wherein the distribution between the three independent scalp sectors is utilized in rendering one or more graphical representations of the patient's brain in the automatically generated cognitive health assessment report.

13. The method of claim 10, wherein the differences for the one or more MMN responses and the one or more N1 responses are based on amplitude, and the differences for the one or more P300 responses is based on both amplitude and latency.

14. The method of claim 10, wherein the data set is transmitted to a display coupled to a computing device, and the method comprises:
normalizing and transforming the determined values into one or more corresponding factors for modifying a visual element corresponding to each determined value,
wherein each factor modifies a size or color of a corresponding visual element.

15. The method of claim 10, wherein the patient is in an unresponsive state and the sensor apparatus is configured to record the brainwave data of the patient during one or more additional rest periods where the patient is not receiving the programmed stimuli.

16. The method of claim 10, wherein the processor is further configured to combine brainwave data of the patient during one or more additional rest periods where the patient is not receiving programmed stimuli with the brainwave data of the patient recorded relating to the presentation of the first or second set of visual or auditory pattern stimuli.

17. The method of claim 10, further comprising controlling rendering of a brain assessment interface including at least a representative mapping of a brain of the patient indicative of one or more areas of the brain that are activated relating to or responsive to the presentation of the first or second set of visual or auditory pattern of programmed stimuli.

18. A non-transitory computer readable medium storing machine interpretable instructions, which when executed by a processor, cause the processor to execute a method for automatically generating a cognitive health assessment report utilizing data sets representative of potential cognitive activity of a patient, the method comprising:

recording, using a sensor apparatus connected to one or more electrodes coupled to the patient's head, the one or more electrodes recording brainwave (EEG) data of the patient in respect of a brain of the patient, a portion of brainwave data of the patient during a first resting period during which no stimulus is being presented to the patient;

processing the brainwave data of the patient to extract one or more waveform features, the one or more waveform features including at least one or more N1, P2, N400, MMN, P300 (P3a/P3b), and N2b responses present in the brainwave data;

controlling a stimulus presentation mechanism to present repeated auditory tones or visual image presentation to the patient;

tracking, by the processor:
one or more N1 and P2 responses to the repeated auditory tones or visual images to measure the brain's processing of auditory stimuli or to measure the brain's processing of visual stimuli;

controlling the stimulus presentation mechanism to present one or more auditory or visual phrases each including one or more nonsensical, or otherwise inaccurate or unexpected portions of a sentence to the patient;

tracking, by the processor:
one or more N400 responses present in the brainwave data during the presentation of the one or more nonsensical, or otherwise inaccurate or unexpected portions of the sentence to measure the brain's ability to process word and phrase meanings, sentence grammar and discourse;

controlling the stimulus presentation mechanism to present one or more incongruous, unexpected or otherwise surprising words or sentences within a language context;

tracking, by the processor:
one or more N400 responses present in the brainwave data during the presentation of the one or more incongruous, unexpected or otherwise surprising words or sentence pairings to track the brain's ability to process word and phrase meanings, and vocabulary recognition;

controlling the stimulus presentation mechanism to present a first set of repeated tones or visuals intermixed with a first set of deviant tones or visuals in concert with a constant tone or visual; and tracking, by the processor:
one or more MMN responses present in the brainwave data during the presentation of the first set of one or more deviant tones or visuals to track the brain's ability to respond to environmental changes that are not actively attended;

controlling the stimulus presentation mechanism to present a second set of repeated tones or visuals intermixed with a second set of deviant tones or visuals;

tracking, by the processor:
one or more P3a responses present in the brainwave data during the presentation of the one or more deviant tones or visuals to track the brain's ability to respond to stimulus deviance;

controlling the stimulus presentation mechanism to present the second set of repeated tones or visuals intermixed with the second set of deviant tones or visuals and to automatically present instructions rendered on a computer screen or generate audible instructions instructing the patient to actively recognize or respond to the second set of deviant tones or visuals;

tracking, by the processor:
one or more P3b responses present in the brainwave data during the presentation of the second set of deviant tones or visuals to track the brain's ability to focus one's attention on a task;

controlling the stimulus presentation mechanism to present a first set of visual or auditory pattern stimuli, at least one stimuli of which are repeated throughout the first set of visual or auditory pattern stimuli and to automatically present instructions rendered on the computer screen or generate audible instructions instructing the patient to actively recognize or respond to the repeated stimuli in the first set of visual or auditory pattern stimuli;

tracking, by the processor:
one or more P3b responses present in the brainwave data during the presentation of the first set of visual or auditory pattern stimuli to track the brain's ability to temporarily hold information available for processing;

controlling the stimulus presentation mechanism to present a second set of visual or auditory pattern stimuli, at least one stimuli of which are repeated throughout the second set of visual or auditory pattern stimuli and to automatically present instructions rendered on the computer screen or generate audible instructions instructing the patient to actively ignore the specific visuals or auditory tones or patterns, and recognize or respond to the alternate repeated visuals or auditory tones or patterns in the second set of visual or auditory pattern stimuli;

tracking, by the processor:
one or more N2b responses present in the brainwave data during the presentation of the second set of visual or auditory pattern stimuli to track the brain's ability to work through processes to enable behaviour;

respective differences in amplitude or latency of the N1, P2, N400, MMN, P300 (P3a/P3b), and N2b responses relative to corresponding responses in a control group; and the one or more P3b responses;

determining, data fields corresponding to at least one of an automatic attention value based at least on the differences in the one or more MMN responses, a reactive attention value based at least on the differences in the one or more P3a responses, a concentration value based on at least the differences in the one or more P3b responses, a working memory value based at least on the differences in the one or more P3a responses, or an executive function value based at least on the differences in the one or more N2b responses;

encapsulating as a data set into a data structure representing the cognitive health assessment report the at least one of the automatic attention value, the reactive attention value, the concentration value, the working memory value, or the executive function value; and automatically generating and presenting, to an individual on a graphical user interface, the cognitive health assessment report generated based on the data set;

wherein the patient is elderly, disabled, diagnosed with a potential concussion or acquired brain injuries, is in an unresponsive state or is comatose.

* * * * *